US012702675B2

(12) United States Patent
Holland et al.

(10) Patent No.: US 12,702,675 B2
(45) Date of Patent: Aug. 11, 2026

(54) TETRAHYDROCOCANNABINOLIC ACID COCRYSTALS

(71) Applicant: Manoira Corporation, Tuxedo Park, NY (US)

(72) Inventors: Joanne Holland, Cambridge (GB); Alex Eberlin, Cambridge (GB); Christopher Frampton, Suffolk (GB)

(73) Assignee: MANOIRA CORPORATION, Tuxedo Park, NY (US)

( * ) Notice: Subject to any disclaimer, the term of this patent is extended or adjusted under 35 U.S.C. 154(b) by 0 days.

(21) Appl. No.: 17/999,315

(22) PCT Filed: May 17, 2021

(86) PCT No.: PCT/IB2021/000331

§ 371 (c)(1),
(2) Date: Nov. 18, 2022

(87) PCT Pub. No.: WO2021/234449

PCT Pub. Date: Nov. 25, 2021

(65) Prior Publication Data

US 2023/0183202 A1 Jun. 15, 2023

Related U.S. Application Data

(60) Provisional application No. 63/026,835, filed on May 19, 2020.

(51) Int. Cl.

| | |
|---|---|
| ***C07D 311/80*** | (2006.01) |
| ***A61K 31/00*** | (2006.01) |
| ***C07D 473/12*** | (2006.01) |

(52) U.S. Cl.

CPC .......... *A61K 31/658* (2023.05); *C07D 311/80* (2013.01); *C07D 473/12* (2013.01); *C07B 2200/13* (2013.01)

(58) Field of Classification Search

CPC .. C07D 311/80; C07D 473/12; C07B 2200/13
USPC ...................................................... 514/263.2
See application file for complete search history.

(56) References Cited

U.S. PATENT DOCUMENTS

2017/0008870 A1 1/2017 Dibble et al.

FOREIGN PATENT DOCUMENTS

| | | |
|---|---|---|
| WO | 2019/030158 A1 | 2/2019 |
| WO | 2019/118360 A1 | 6/2019 |
| WO | 2020/089424 A1 | 5/2020 |

OTHER PUBLICATIONS

International Search Report for PCT International Application No. PCT/IB2021/000331, dated Sep. 3, 2021.

McPartland, J.M. et al., "Affinity and Efficacy Studies of Tetrahydrocannabinolic Acid A at Cannabinoid Receptor Types One and Two", Cannabis and Cannabinoid Research, 2.1 (2017) pp. 89-95.

Moreno-Sanz, G., "Can You Pass the Acid Test? Critical Review and Novel Therapeutic Perspectives of D9-Tetrahydrocannabinolic Acid A", Cannabis and Cannabinoid Research, 1.1 (2016) pp. 124-130.

Shan N. et al., "Impact of pharmaceutical cocrystals: the effects on drug pharmacokinetics", Expert Opinion on Drug Metabolism & Toxicology, 10(9) (2014) pp. 1255-1271.

Tilborg, A. et al., "Pharmaceutical salts and cocrystals involving amino acids: A brief structural overview of the state-of-art", European Journal of Medicinal Chemistry, 74 (2014) pp. 411-426.

Skell, J.M. et al., "Delta9-Tetrahydrocannabinolic acid A, the precursor to Delta9-tetrahydrocannabinol (THC)" Acta Cryst., C77 (2021) pp. 84-89.

*Primary Examiner* — Kristin A Vajda

(74) *Attorney, Agent, or Firm* — Calfee, Halter & Griswold LLP

(57) ABSTRACT

New tetrahydrocannabinolic acid cocrystals are disclosed, in particular, a 1:1 tetrahydrocannabinolic acid L-proline cocrystal, a 1:1 tetrahydrocannabinolic acid D-proline cocrystal, a 1:1 tetrahydrocannabinolic acid D,L-proline cocrystal, a 1:1 tetrahydrocannabinolic acid ethyl maltol cocrystal and a 1:1 tetrahydrocannabinolic acid caffeine cocrystal. The invention also relates to pharmaceutical compositions containing a tetrahydrocannabinolic acid cocrystal of the invention and a pharmaceutically acceptable carrier and methods to treat a disease, disorder or condition by administering to a patient in need thereof a therapeutically effective amount of tetrahydrocannabinolic acid cocrystal or a pharmaceutical composition containing a tetrahydrocannabinolic acid cocrystal.

7 Claims, 18 Drawing Sheets

Heat Flow Endo Up (mW)
21.04
20
19
18
17
16
15
14
13
12
11
10.17
Temperature (°C)
30
40
60
80
100
120
140
160
180
200

TETRAHYDROCOCANNABINOLIC ACID COCRYSTALS

CROSS-REFERENCE TO RELATED APPLICATIONS

This application claims priority to U.S. application No. 63/026,835, filed May 19, 2020, which is incorporated by reference.

FIELD OF THE INVENTION

The invention relates to tetrahydrocannabinolic acid cocrystals, therapeutic uses of the tetrahydrocannabinolic acid cocrystals and pharmaceutical compositions containing them.

BACKGROUND

In recent years there has been growing interest in the pharmacological properties of the cannabinoids that can be found in *cannabis* due to their potential application in a wide range of pathological conditions. Even though 113 different cannabinoids can be present in *cannabis*, on extraction the majority of the extract consists of the two cannabinoids tetrahydrocannabinol (THC) and cannabidiol (CBD). Therefore, most of the research to date has been centered on these two cannabinoids. However, THC has a major limitation in its pharmaceutical use due to its CB1 receptor agonism leading to psychoactive effects. In the *cannabis* plant itself all the cannabinoids exist in their acidic forms, so tetrahydrocannabinol instead exists as tetrahydrocannabinolic acid (THCA) in the *cannabis* plant. Extraction methods typically result in the decarboxylation of THCA to THC, especially if heat is involved. THCA itself is devoid of psychoactive side effects but it does have many potential pharmaceutical applications of its own making it a compound of pharmaceutical interest. Although in theory THCA can exist in two different isomeric forms THCA-A and THCA-B, shown below, most *cannabis* plants produce only THCA-A. Therefore, when the abbreviation THCA is used in literature it typically refers solely to THCA-A. The inventions disclosed herein refer solely to THCA-A, therefore using standard terminology tetrahydrocannabinolic acid isomer A (THCA-A) is referred to as tetrahydrocannabinolic acid (THCA) throughout.

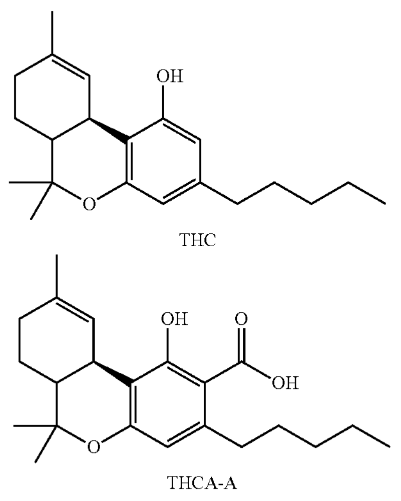

THC

THCA-A

-continued

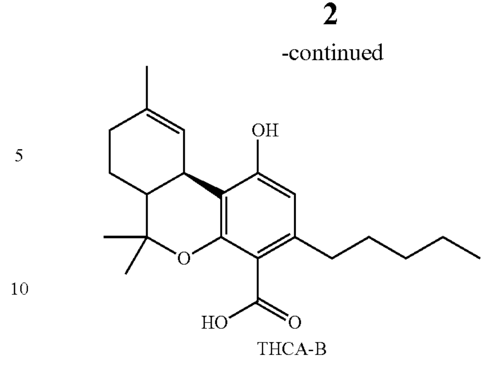

THCA-B

Initial research has shown that THCA may possess anti-inflammatory properties, neuroprotective properties, anti-emetic properties and anti-proliferative properties. THCA also may have potential in the treatment of disorders or the symptoms of disorders such as seizures (including epilepsy), pain, diabetes, adiposity and metabolic syndrome.

Despite the numerous potential pharmaceutical applications of THCA, it is widely documented in literature that THCA readily decarboxylates to THC on storage especially under conditions of heat or light. J. M. McPartland, *Cannabis and Cannabinoid Research,* 2017; 2(1): 87-95. This suggests that contamination of THCA with THC is almost inevitable. This has hampered both the pharmacological exploration and clinical use of THCA. There is, therefore, a need to develop new forms of THCA that are stable upon storage to allow the potential of THCA to be fully explored.

Although therapeutic efficacy is the primary concern for an active pharmaceutical ingredient (API), the chemical composition and solid-state form (i.e., the crystalline or amorphous form) of the API can be critical to its pharmacological properties, such as bioavailability, and to its development as a viable drug candidate. Compositions and crystalline forms of some API's have been used to alter the API's physicochemical properties. Each composition or crystalline form can have different solid state (physical and chemical) properties. The differences in physical properties exhibited by a novel solid-state forms (such as, for example, a polymorph of the API or a cocrystal containing the API, discussed below) may affect pharmaceutical and pharmacological properties such as storage stability, compressibility and density (important in formulation and product manufacturing), and/or solubility and dissolution rates (important factors in determining bioavailability). For example, the rate of dissolution of an active ingredient in a patient's stomach fluid may have therapeutic consequences since it impacts the rate at which an orally administered active ingredient may reach the patient's bloodstream. Because these practical properties are influenced by the solid-state properties, e.g. the crystalline form of the API, they can impact the selection of a particular compound as an API, the ultimate pharmaceutical dosage form, the optimization of manufacturing processes, and absorption in the body.

Physical properties of an API also have a major influence on the ability to deliver a drug by a desired method. For example, if a drug is delivered by inhalation physical properties relating to the API as a particle, such as morphology, density, surface energy, charge, hygroscopicity, stability, dispersive properties and/or agglomeration, can come into play. The solid-state form of the API, and as described below, cocrystals of the API, provide opportunities to address, engineer and/or improve upon one or more of such properties and thereby upon methods of delivery.

Obtaining crystalline forms of an API, when possible, is also extremely useful in drug development. It permits better characterization of the drug candidate's chemical and physical properties. Crystalline forms often have better chemical and physical properties than the API in its amorphous state. Moreover; finding the most adequate solid-state form for further drug development can reduce the time and the cost of that development.

It may be possible to achieve more desirable properties of a particular API by forming a cocrystal of the API. A cocrystal of an API is a distinct chemical composition of the API and coformer(s) and generally possesses distinct crystallographic and spectroscopic properties when compared to those of the API and coformer(s) individually. Crystallographic and spectroscopic properties of crystalline forms are typically measured by X-ray powder diffraction (XRPD) and single crystal X-ray crystallography, among other techniques. Cocrystals often also exhibit distinct thermal behavior. Thermal behavior is measured in the laboratory by such techniques as capillary melting point, thermogravimetric analysis (TGA) and differential scanning calorimetry (DSC). Cocrystals often possess more favorable solid state, physical, chemical, pharmaceutical and/or pharmacological properties or be easier to process than known forms or formulations of the API. For example, a cocrystal may have different dissolution and/or solubility properties than the API and can therefore be more effective in therapeutic delivery. Formation of a cocrystal can be used as a way to avoid polymorph formation of the drug. New pharmaceutical compositions comprising a cocrystal of a given API may therefore have different or superior properties as compared to its existing drug formulations.

Unlike salts, which possess a neutral net charge, but which are comprised of charge-balanced components, cocrystals are comprised of neutral species. Thus, unlike a salt, one cannot determine the stoichiometry of a cocrystal based on charge balance. Indeed, one can often obtain cocrystals having stoichiometric ratios of drug to coformer of greater than or less than 1:1. The stoichiometric ratio of an API to coformer is a generally unpredictable feature of a cocrystal.

Without limiting the disclosed invention to any particular definition because others may define the term differently, the term 'cocrystal' may be thought of as a multi-component crystal composed of neutral molecules. These multi-component assemblies are continuing to excite and find usefulness, particularly within the pharmaceutical field, for their ability to alter physicochemical properties. More specifically, cocrystals have been reported to alter melting point, aqueous solubility and/or dissolution rates, increase stability and improve bioavailability of active pharmaceutical ingredients.

SUMMARY OF THE INVENTION

The invention relates to new tetrahydrocannabinolic acid cocrystals. In particular, the invention relates to a 1:1 tetrahydrocannabinolic acid L-proline cocrystal, a 1:1 tetrahydrocannabinolic acid D-proline cocrystal, a 1:1 tetrahydrocannabinolic acid D,L-proline cocrystal, a 1:1 tetrahydrocannabinolic acid ethyl maltol cocrystal and a 1:1 tetrahydrocannabinolic acid caffeine cocrystal. The invention also relates to pharmaceutical compositions containing a tetrahydrocannabinolic acid cocrystal of the invention and a pharmaceutically acceptable carrier. The tetrahydrocannabinolic acid cocrystals of the invention may be used in the same way as tetrahydrocannabinolic acid. Tetrahydrocannabinolic acid possesses anti-inflammatory, neuroprotective, anti-emetic and anti-proliferative properties and may have potential in the treatment of disorders or the symptoms of disorders such as seizures (including epilepsy), pain, diabetes, adiposity and metabolic syndrome. The tetrahydrocannabinolic acid cocrystals of the invention as such may be useful for the treatment of the diseases, disorders and conditions associated with such properties.

DETAILED DESCRIPTION

Figure 1:
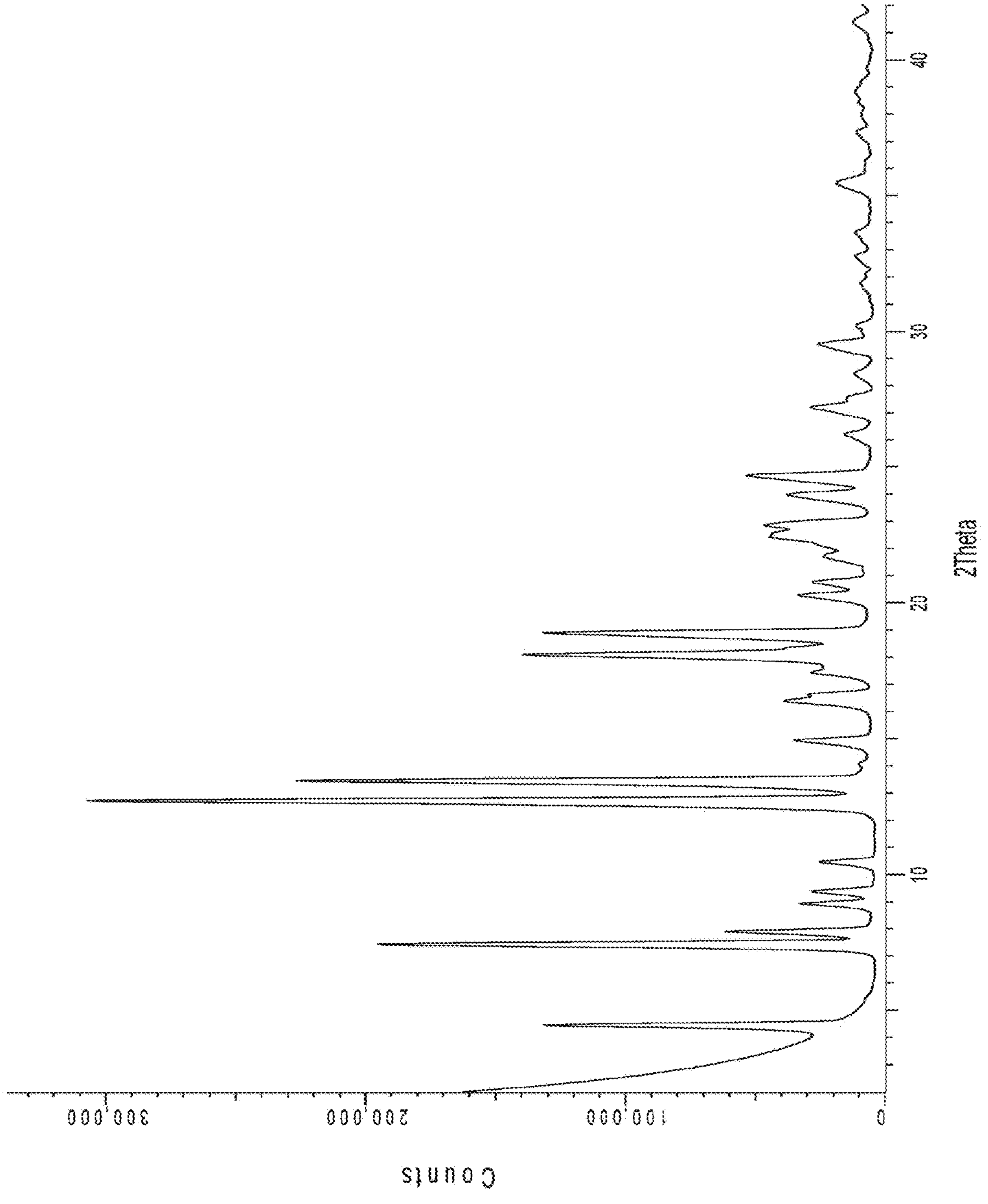
FIG. 1 shows a low resolution XRPD diagram of the 1:1 tetrahydrocannabinolic acid L-proline cocrystal.

The invention relates to new tetrahydrocannabinolic acid cocrystals. In particular, the invention relates to a 1:1 tetrahydrocannabinolic acid L-proline cocrystal, a 1:1 tetrahydrocannabinolic acid D-proline cocrystal, a 1:1 tetrahydrocannabinolic acid D,L-proline cocrystal, a 1:1 tetrahydrocannabinolic acid ethyl maltol cocrystal and a 1:1 tetrahydrocannabinolic acid caffeine cocrystal. These tetrahydrocannabinolic acid cocrystals of the invention, their preparation and their characterization are described in the examples below and shown in the figures. The invention relates to pharmaceutical compositions containing a therapeutically effective amount of a tetrahydrocannabinolic acid cocrystal of the invention and a pharmaceutically acceptable carrier. The invention also relates to methods of treatment for the diseases, disorders and conditions described herein and the use of a therapeutically effective amount of a tetrahydrocannabinolic acid cocrystal of the invention, or a pharmaceutical composition containing it, for that treatment. The invention further provides the use of a tetrahydrocannabinolic acid cocrystal of the invention in the manufacture of a medicament for use in the treatment of the diseases, disorders and conditions described herein.

Therapeutic Uses of Tetrahydrocannabinic Acid Cocrystals

As discussed above tetrahydrocannabinolic acid is known in the art to be useful in the treatment of various diseases, disorders and conditions. The tetrahydrocannabinolic acid cocrystals of the invention, 1:1 tetrahydrocannabinolic acid L-proline cocrystal, 1:1 tetrahydrocannabinolic acid D-proline cocrystal, 1:1 tetrahydrocannabinolic acid D,L-proline cocrystal, 1:1 tetrahydrocannabinolic acid ethyl maltol cocrystal and 1:1 tetrahydrocannabinolic acid caffeine cocrystal, and pharmaceutical compositions containing them may then also be used to treat such diseases, disorders and conditions. The diseases, disorders or conditions which may treated with a tetrahydrocannabinolic acid cocrystal of the invention include, but are not limited to: pain (including but not limited to acute pain; chronic pain; neuropathic pain and cancer pain), neurodegenerative disease (including but not limited to Alzheimer's disease; Parkinson's disease; amyotrophic lateral sclerosis; Huntington's disease; multiple sclerosis; frontotemporal dementia; prion disease; Lewy body dementia; progressive supranuclear palsy; vascular dementia; normal pressure hydrocephalus; traumatic spinal cord injury; HIV dementia; alcohol induced neurotoxicity; Down's syndrome; epilepsy or any other related neurological or psychiatric neurodegenerative disease), inflammatory or autoimmune disease, fibrosis, cancer, nausea and vomiting, diabetes, adiposity and metabolic syndrome.

Accordingly, the invention relates to the method of treating such a disease, disorder, or condition comprising the step of administering to a patient in need thereof a therapeutically effective amount of a tetrahydrocannabinolic acid cocrystal of the invention or of administering to a patient in need thereof a therapeutic composition containing a tetrahydrocannabinolic acid cocrystal of the invention.

The term "treatment" or "treating" means any treatment of a disease, disorder or condition in a mammal, including: preventing or protecting against the disease, disorder or condition, that is, causing the clinical symptoms not to develop; inhibiting the disease, disorder or condition, that is, arresting or suppressing the development of clinical symptoms; and/or relieving the disease, disorder or condition (including the relief of discomfort associated with the condition or disorder), that is, causing the regression of clinical symptoms. It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" the disease, disorder or condition. The term "protection" is meant to include "prophylaxis."

Another aspect of the invention relates to the use of a tetrahydrocannabinolic acid cocrystal of the invention in the treatment of diseases, disorders and conditions discussed above. Accordingly, the invention further relates to the manufacture of a medicament for use in the treatment of such diseases, disorders and conditions.

Pharmaceutical Compositions Containing Tetrahydrocannabinolic Acid Cocrystals

The invention relates to pharmaceutical compositions comprising, consisting essentially or consisting of a therapeutically effective amount of a tetrahydrocannabinolic acid cocrystal according to the invention and a pharmaceutically acceptable carrier (also known as a pharmaceutically acceptable excipient). As mentioned above, these pharmaceutical compositions are therapeutically useful to treat or prevent disorders such as those discussed above. A pharmaceutical composition of the invention may be a solid dosage form or a solution made with a tetrahydrocannabinolic acid cocrystal of the invention.

A pharmaceutical composition of the invention may be in any pharmaceutical form which contains a tetrahydrocannabinolic acid cocrystal according to the invention. The pharmaceutical composition may be, for example, a tablet, a capsule, an oral solution, an injectable composition, a topical composition, an inhalable composition or a transdermal composition. Liquid pharmaceutical compositions may be prepared using a tetrahydrocannabinolic acid cocrystal of the invention and represent a particular embodiment of the invention. For a liquid pharmaceutical composition, the tetrahydrocannabinolic acid cocrystal may be dissolved in a solvent, e.g. water, at the time and point of care.

The pharmaceutical compositions generally contain, for example, about 0.1% to about 99.9% by weight of a tetrahydrocannabinolic acid cocrystal of the invention, for example, about 0.5% to about 99% by weight of a tetrahydrocannabinolic acid cocrystal of the invention and, for example, 99.5% to 0.5% by weight of at least one suitable pharmaceutical excipient or solvent. In one embodiment, the composition may be between about 5% and about 75% by weight of a tetrahydrocannabinolic acid cocrystal of the invention with the rest being at least one suitable pharmaceutical excipient, solvent or at least one other adjuvant, as discussed below.

A "therapeutically effective amount of a tetrahydrocannabinolic acid cocrystal according to the invention" is that which correlates to a therapeutic effect and may for example, be about 5 mg-about 2,000 mg, about 50 mg-about 1500 mg, about 100 mg-about 1000 mg, about 250 mg-about 750 mg, or about 500 mg. The actual amount required for treatment of any particular disease, disorder or condition for any particular patient may depend upon a variety of factors including, for example, the particular disease, disorder or condition being treated; the disease state being treated and its severity; the specific pharmaceutical composition employed; the age, body weight, general health, sex and diet of the patient; the mode of administration; the time of administration; the route of administration; and the rate of excretion; the duration of the treatment; any drugs used in combination or coincidental with the specific compound employed; and other such factors well known in the medical arts. These factors are discussed in Goodman and Gilman's "The Pharmacological Basis of Therapeutics", Tenth Edition, A. Gilman, J. Hardman and L. Limbird, eds., McGraw-Hill Press, 155-173, 2001, which is incorporated herein by reference.

Depending on the type of pharmaceutical composition, the pharmaceutically acceptable carrier may be chosen from any one or a combination of carriers known in the art. The choice of pharmaceutically acceptable carrier depends upon the pharmaceutical form and the desired method of administration to be used. For a pharmaceutical composition of the invention, that is one containing a tetrahydrocannabinolic acid cocrystal of the invention, a carrier should be chosen that maintains the crystalline form. In other words, the carrier should not substantially alter the tetrahydrocannabinolic acid cocrystal. Nor should the carrier be otherwise incompatible with a tetrahydrocannabinolic acid cocrystal used, such as by producing any undesirable biological effect or otherwise interacting in a deleterious manner with any other component(s) of the pharmaceutical composition.

The pharmaceutical compositions of the invention may be prepared by methods known in the pharmaceutical formulation art, for example, see Remington's Pharmaceutical Sciences, 18th Ed., (Mack Publishing Company, Easton, Pa., 1990), which is incorporated herein by reference. In a solid dosage form, a tetrahydrocannabinolic acid cocrystal of the invention may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alginates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Pharmaceutically acceptable adjuvants known in the pharmaceutical formulation art may also be used in the pharmaceutical compositions of the invention. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others, as is known in the pharmaceutical art. They may contain pacifying agents and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Liquid dosage forms may be aqueous, may contain a pharmaceutically acceptable solvent as well as traditional liquid dosage form excipients known in the art which include, but are not limited to, buffering agents, flavorants, sweetening agents, preservatives, and stabilizing agents.

A pharmaceutical composition of the invention may be formulated as a chewable lozenge, also known as a gummy-type lozenge. As is known in the art, chewable lozenge formulations may be prepared from glycerin, gelatin, and water. The lozenges typically also contain a flavorant such as a fruit or candy flavor and a colorant to give the formulation a pleasant flavor and appearance. Chewable lozenges may also be made or molded into a variety of shapes such as, but not limited to, ovoid, spherical, platonic solids (e.g. tetrahedrons, cubes, octahedrons, etc.), rectangular prisms, cones, pyramids, cylinders, fruit slices, animals, cartoon characters, cars, etc. An exemplary chewable lozenge of the invention may contain: a desired amount of the cocrystal, glycerin, gelatin, water, methylparaben, flavoring oil, and a colorant.

A pharmaceutical composition of the invention may also be formulated as a sublingual or buccal preparation—a tablet form not used as often as oral tablets. These small, hard compressed tablets are designed to dissolve rapidly in the vascular mucous membrane of the mouth. Buccal tablets are placed in the buccal pouch (between the check and the gum) and sublingual tablets are placed under the tongue. Because the buccal and sublingual areas are highly vascularized, drugs are quickly absorbed into the bloodstream with rapid onset of the drug effects. Drugs administered in this way avoid first-pass metabolism because the adsorbed drug bypasses the portal vein unlike drugs adsorbed from the gastrointestinal (GI) tract. Sublingual and buccal formulations may be prepared using pharmaceutically acceptable carriers and disintegrants known in the art as well as flavorants and other additives to improve taste and patient acceptance and compliance.

Inhalable formulations may be used to administer a tetrahydrocannabinolic acid cocrystal of the invention topically to the lung or within the nasal passages. One inhalable formulation is a dry powder inhaler formulation of respirable particles comprised of a tetrahydrocannabinolic acid cocrystal of the invention, which the patient being treated inhales. It is common for a dry powder formulation to include carrier particles, to which the cocrystal particles can adhere to. The carrier particles may be of any acceptable pharmacologically inert material or combination of materials. For example, the carrier particles may be composed of one or more materials selected from sugar alcohols; polyols, for example sorbitol, mannitol or xylitol, and crystalline sugars, including monosaccharides and disaccharides; inorganic salts such as sodium chloride and calcium carbonate; organic salts such as sodium lactate; and other organic compounds such as urea, polysaccharides, for example cyclodextrins and dextrins. The carrier particles may be a crystalline sugar, for example, a monosaccharide such as glucose or arabinose, or a disaccharide such as maltose, saccharose, dextrose or lactose. The cocrystal would be dispersed into the respiratory tract in a pharmaceutically effective amount.

Compositions for rectal administrations are, for example, suppositories that may be prepared by mixing a tetrahydrocannabinolic acid cocrystal of the invention with, for example, suitable non-irritating excipients or carriers such as cocoa butter, polyethyleneglycol or a suppository wax, which may be solid at ordinary temperatures but may be liquid at body temperature and, therefore, melt while in a suitable body cavity and release the active component therein.

Compositions suitable for topical administration include liquid or semi-liquid preparations such as liniments, lotions, gels, applicants, oil-in-water or water-in-oil emulsions such as creams, ointments, pastes or foams; or solutions or suspensions such as drops, as is known in the art. Compositions of the invention may be intended for topical administration, in which case the carrier may suitably comprise a solution, emulsion, ointment or gel base. The carrier or base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

In addition to the topical method of administration described above, there are various methods of administering the active a tetrahydrocannabinolic acid cocrystal of the invention topically to the lung. One such means could involve a dry powder inhaler formulation of respirable particles comprised of a tetrahydrocannabinolic acid cocrystal of the invention, which the patient being treated inhales. It is common for a dry powder formulation to include carrier particles, to which tetrahydrocannabinolic acid cocrystal particles can adhere to. The carrier particles may be of any acceptable pharmacologically inert material or combination of materials. For example, the carrier particles may be composed of one or more materials selected from sugar alcohols; polyols, for example sorbitol, mannitol or xylitol, and crystalline sugars, including monosaccharides and disaccharides; inorganic salts such as sodium chloride and calcium carbonate; organic salts such as sodium lactate; and other organic compounds such as urea, polysaccharides, for example cyclodextrins and dextrins. The carrier particles may be a crystalline sugar, for example, a monosaccharide such as glucose or arabinose, or a disaccharide such as maltose, saccharose, dextrose or lactose.

In addition to the topical method of administration described above, there are various methods of administering the active a tetrahydrocannabinolic acid cocrystal of the invention systemically by such methods. One such means would involve an aerosol suspension of respirable particles comprised of a tetrahydrocannabinolic acid cocrystal of the invention, which the patient being treated inhales. A tetrahydrocannabinolic acid cocrystal would be absorbed into the bloodstream via the lungs in a pharmaceutically effective amount. The respirable particles can be liquid or solid, with a particle size sufficiently small to pass through the mouth and larynx upon inhalation.

Because the crystalline form of a tetrahydrocannabinolic acid cocrystal may be maintained during preparation, solid dosage forms are one embodiment of the pharmaceutical composition of the invention. Dosage forms for oral administration, which includes capsules, tablets, pills, powders, granules, and suspensions may be used. Dosage forms for pulmonary administration, which includes metered dose inhaler, dry powder inhaler or aerosol formulations may be used. In such solid dosage forms, the active compound may be mixed with at least one inert, pharmaceutically acceptable excipient (also known as a pharmaceutically acceptable carrier).

A tetrahydrocannabinolic acid cocrystal according to the invention may also be used to formulate liquid or injectable pharmaceutical compositions. Administration of a tetrahydrocannabinolic acid cocrystal in pure form or in an appropriate pharmaceutical composition may be carried out via any of the accepted modes of administration or agents for serving similar utilities. Thus, administration may be, for example, orally, buccally, nasally, pulmonary, parenterally (intravenous, intramuscular, or subcutaneous), topically, transdermally, intravaginally, intravesically, intrasystemically, ophthalmically or rectally, in the form of solid, semisolid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the condition to be treated.

The invention also relates to a method of preparing a liquid pharmaceutical composition comprising the step of dissolving a tetrahydrocannabinolic acid cocrystal according to the invention in a pharmaceutically acceptable solvent and to liquid pharmaceutical compositions prepared according to that method. As discussed above, liquid pharmaceutical compositions of the invention may be administered orally, parenterally (including by inhalation), and intravenously.

EXAMPLES

The following analytical methods were used to characterize the tetrahydrocannabinolic acid cocrystals of the invention:

Low Resolution X-Ray Powder Diffraction Characterisation: Low resolution X-ray powder diffraction patterns for the samples were acquired on a Bruker 2nd Gen D2-Phaser diffractometer using CuKα radiation (30V, 1.0 mA), θ-2θ goniometer, V4 receiving slits, a Ge monochromator and a Lynxeye detector. The instrument is performance checked using a certified Corundum standard (NIST 1976). The data were collected at ambient temperature over an angular range of 2° to 35° 2θ (using a step size of 0.05° 2θ and a step time of 2.0 seconds) or an angular range of 2° to 42° 2θ (using a step size of 0.025° 2θ and a step time of 5.0 seconds). Samples run under ambient conditions were prepared as flat plate specimens using powder as received without grinding. Approximately, 20 mg of the sample was gently packed into sample holder and all samples were analysed using Diffrac Plus EVA v4.2.0.14

High Resolution X-Ray Powder Diffraction Characterisation: High Resolution XRPD diffractograms were collected on a Bruker D8 diffractometer using Cu Ka radiation (40 kV, 40 mA) and a θ-2θ goniometer fitted with a Ge monochromator. The incident beam passes through a 2.0 mm divergence slit followed by a 0.2 mm antiscatter slit and knife edge. The diffracted beam passes through an 8.0 mm receiving slit with 2.5° Soller slits followed by the Lynxeye Detector. The software used for data collection and analysis was Diffrac Plus XRD Commander and Diffrac Plus EVA respectively. Samples were run under ambient conditions over an angular range of 2° to 42° 2θ (using a step size of 0.05° 20 and a step time of 0.5 seconds) as flat plate specimens using powder as received. The sample was prepared on a polished, zero-background (510) silicon wafer by gently pressing onto the flat surface or packed into a cut cavity. The sample was rotated in its own plane.

Single Crystal X-Ray Diffraction (SCXRD): Data were collected on an Oxford Diffraction SuperNova Dual source, Cu at zero, Atlas CCD Diffractometer equipped with an Oxford Cryosystems Cryostream cooling device. Structures were solved using the Bruker SHELXTL program and refined with the SHELXTL program as part of the Bruker SHELXTL suite. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

Thermal Analysis—Differential Scanning calorimetry (DSC): DSC data were collected on a PerkinElmer Pyris 4000 DSC equipped with a 45 position sample holder. The instrument was verified for energy and temperature calibration using certified indium. A predefined amount of the sample, 0.5-3.0 mg, was placed in a pin holed aluminium pan and heated at 20° C.·$min^{-1}$ from 30 to 350° C. A purge of dry nitrogen at 60 ml·$min^{-1}$ was maintained over the sample. The instrument control, data acquisition and analysis were performed with Pyris Software v9.0.1.0203.

Thermo-Gravimetric Analysis (TGA): TGA data were collected on a PerkinElmer Pyris 1 TGA equipped with a 20 position auto-sampler. The instrument was calibrated using a certified weight and certified Alumel and Perkalloy for temperature. A predefined amount of the sample, 1-5 mg, was loaded onto a pre-tared aluminium crucible and was heated at 20° C.·$min^{-1}$ from ambient temperature to 400° C. A nitrogen purge at 20 ml·$min^{-1}$ was maintained over the sample. The instrument control, data acquisition and analysis were performed with Pyris Software v9.0.1.0203.

Solution Proton NMR: $^1$H-NMR spectra were collected using a JEOL EX 270 MHz spectrometer equipped with an auto-sampler. The samples were dissolved in d6-DMSO for analysis. The data was acquired using Delta NMR Processing and Control Software version 4.3.

Example 1: 1:1 Tetrahydrocannabinolic Acid L-Proline Cocrystal

1.1 Preparation of a 1:1 Tetrahydrocannabinolic Acid L-Proline Cocrystal

The batch of the 1:1 tetrahydrocannabinolic acid L-proline cocrystal used for characterisation was prepared as follows:

Tetrahydrocannabinolic acid (75 mg, 0.21 mmol) and L-proline (33 mg, 0.28 mmol) were weighed into a glass vial and methanol (1 ml) was added. The resulting white slurry was stirred at room temperature for 30 minutes and then at 5° C. for a further 3 hours. The product was then filtered under vacuum and dried under ambient conditions overnight.

1.2 Low Resolution XRPD Characterisation of a 1:1 Tetrahydrocannabinolic Acid L-Proline Cocrystal The low resolution experimental XRPD pattern of the 1:1 tetrahydrocannabinolic acid L-proline cocrystal is shown in FIG. 1. Table 1 lists the angles, °2θ±0.2°2θ, and d-spacing of the peaks identified in the experimental XRPD pattern of FIG. 1. The entire list of peaks, or a subset thereof, may be sufficient to characterize the cocrystal, as well as by an XRPD pattern substantially similar to FIG. 1. For example, the cocrystal may be characterized by at least two, at least three, at least four or more of the peaks in Table 1 separated from one another by ±0.2° 2θ.

TABLE 1

| Angle °2θ ± 0.2 °2θ | d value Angstrom | Intensity % |
|---|---|---|
| 4.5 | 19.84 | 36.8% |
| 7.4 | 11.89 | 63.2% |
| 7.9 | 11.20 | 18.9% |
| 8.9 | 9.88 | 9.5% |
| 9.4 | 9.41 | 8.0% |
| 10.5 | 8.44 | 7.0% |
| 12.7 | 6.95 | 100.0% |
| 13.5 | 6.58 | 73.4% |
| 14.9 | 5.93 | 9.8% |
| 16.4 | 5.40 | 10.9% |
| 16.6 | 5.33 | 7.8% |
| 17.5 | 5.07 | 6.9% |
| 18.1 | 4.89 | 44.1% |
| 18.9 | 4.69 | 41.4% |
| 20.3 | 4.37 | 8.8% |
| 20.8 | 4.28 | 6.9% |
| 21.7 | 4.09 | 5.7% |
| 22.5 | 3.96 | 12.4% |
| 22.9 | 3.89 | 13.1% |
| 24.0 | 3.71 | 10.4% |
| 24.7 | 3.60 | 15.6% |
| 27.2 | 3.27 | 7.7% |
| 29.5 | 3.02 | 6.9% |

Figure 2:
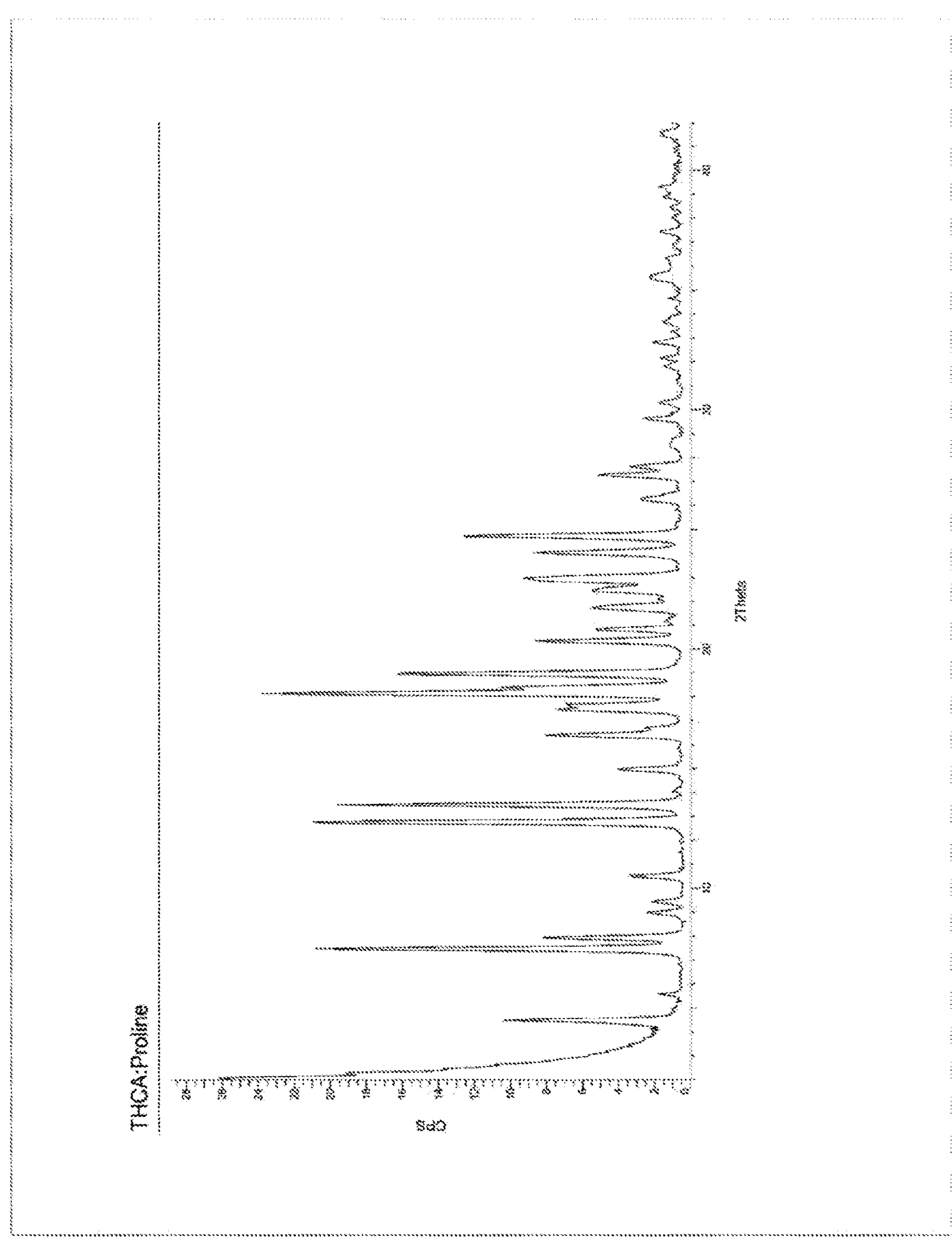
FIG. 2 shows a high resolution XRPD diagram of the 1:1 tetrahydrocannabinolic acid L-proline cocrystal.

1.3 High Resolution XRPD Characterisation of a 1:1 Tetrahydrocannabinolic Acid L-Proline Cocrystal The high resolution experimental XRPD pattern of the 1:1 tetrahydrocannabinolic acid L-proline cocrystal is shown in FIG. 2. Table 2 lists the angles, °2θ±0.2°2θ, and d-spacing of the peaks identified in the experimental XRPD pattern of FIG. 2. The entire list of peaks, or a subset thereof, may be sufficient to characterize the cocrystal, as well as by an XRPD pattern substantially similar to FIG. 2. For example, the cocrystal may be characterized by at least two, at least three, at least four or all of the peaks selected from the peaks at 4.5, 10.5, 12.8, 13.5, 15.0 and 19.0°2θ±0.2°2θ.

TABLE 2

| Angle °2θ ± 0.2 °2θ | d value Angstrom | Intensity % |
|---|---|---|
| 4.5 | 19.63 | 32% |
| 7.5 | 11.81 | 76% |
| 7.9 | 11.12 | 29% |
| 9.0 | 9.83 | 7% |
| 9.4 | 9.36 | 6% |
| 10.5 | 8.41 | 11% |
| 12.8 | 6.92 | 84% |
| 13.5 | 6.56 | 82% |
| 15.0 | 5.91 | 14% |
| 16.4 | 5.4 | 33% |
| 16.7 | 5.31 | 12% |
| 17.5 | 5.07 | 43% |
| 17.7 | 5.02 | 38% |
| 18.1 | 4.89 | 100% |
| 18.4 | 4.83 | 41% |
| 19.0 | 4.68 | 70% |
| 20.3 | 4.36 | 35% |
| 20.8 | 4.26 | 19% |
| 21.8 | 4.08 | 19% |
| 22.5 | 3.95 | 20% |
| 23.0 | 3.87 | 36% |
| 24.0 | 3.7 | 36% |
| 24.7 | 3.6 | 54% |
| 26.3 | 3.39 | 9% |
| 27.3 | 3.27 | 20% |

TABLE 2-continued

| Angle °2θ ± 0.2 °2θ | d value Angstrom | Intensity % |
|---|---|---|
| 27.6 | 3.23 | 12% |
| 29.6 | 3.01 | 9% |
| 30.3 | 2.95 | 6% |

1.4 SCXRD Characterisation of a 1:1 Tetrahydrocannabinolic Acid L-Proline Cocrystal The crystal used for single crystal structure determination was prepared as follows:

Tetrahydrocannabinolic acid (57 mg, 0.16 mmol) and L-proline (18.5 mg, 0.16 mmol) were weighed into a glass vial and methanol (0.8 ml) was added. The resulting white slurry was stirred at 5° C. for 1 hr. The white precipitate was filtered and air dried for 15 minutes. A suitable crystal was selected and the structure determined.

Figure 3:
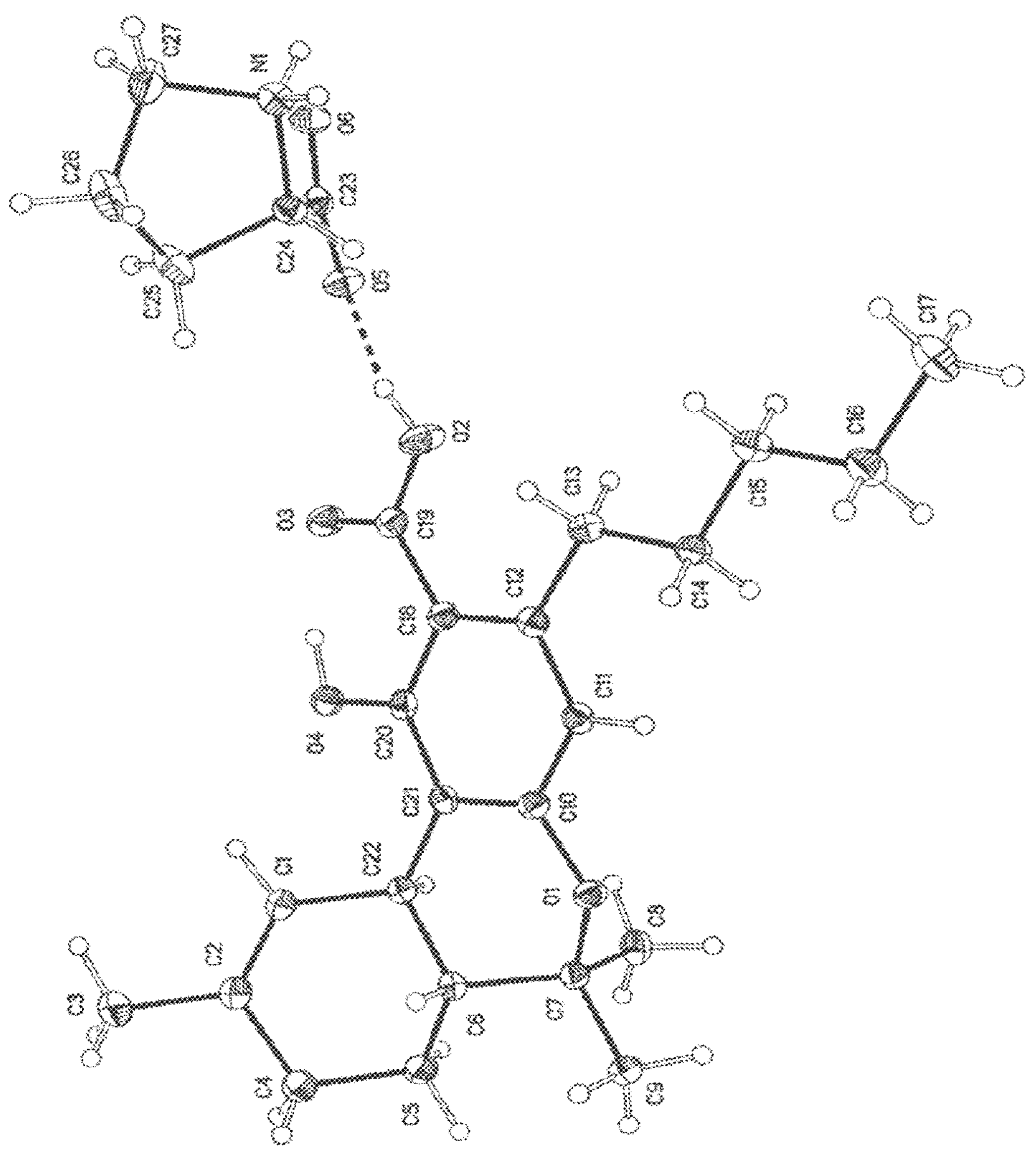
FIG. 3 shows an ORTEP drawing of the 1:1 tetrahydrocannabinolic acid L-proline cocrystal at 100 K.
Figure 4:
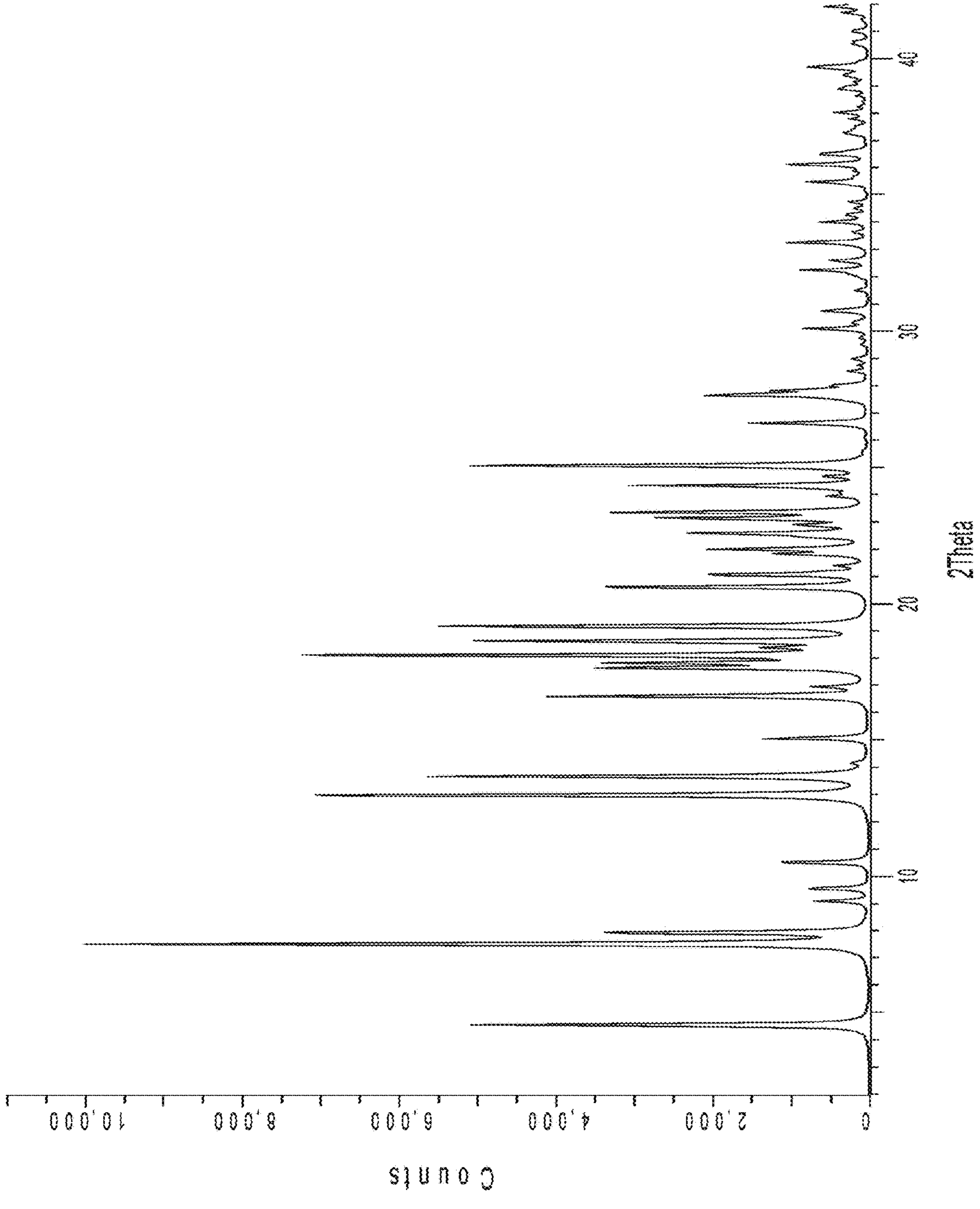
FIG. 4 shows a calculated XRPD pattern for the 1:1 tetrahydrocannabinolic acid L-proline cocrystal at 100 K.
Figure 5:
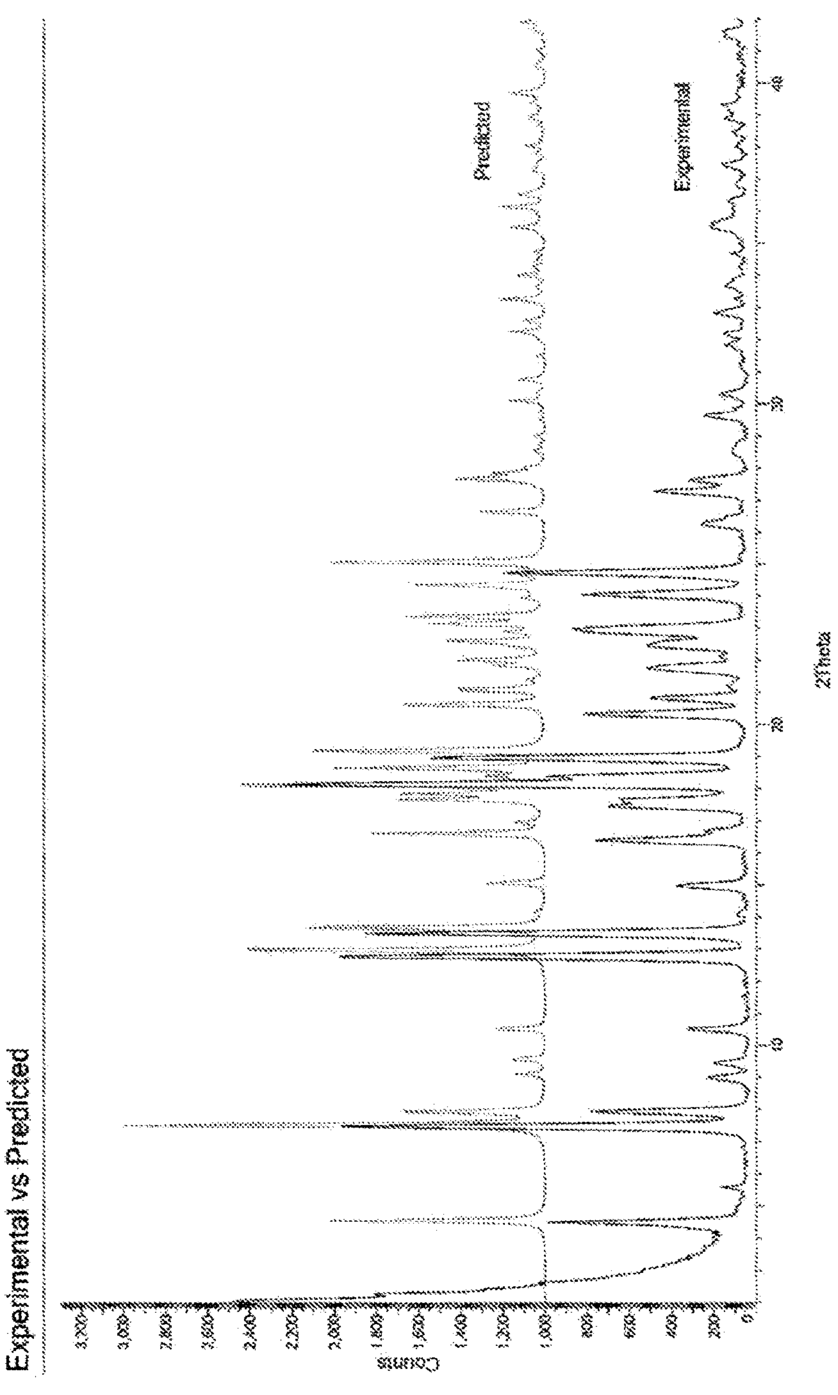
FIG. 5 shows an overlay of the experimental high resolution XRPD pattern for the 1:1 tetrahydrocannabinolic acid L-proline cocrystal at 298K (bottom) with the calculated/predicted XRPD pattern at 100K (top).

The single crystal data and structure refinement parameters for the structure measured at 100 K are reported in Table 3, below. An ORTEP diagram of the 1:1 tetrahydrocannabinolic acid L-proline cocrystal at 100 K showing the numbering system employed is shown in FIG. 3. Anisotropic atomic displacement ellipsoids for the non-hydrogen atoms are shown at the 50% probability level and hydrogen atoms are displayed as spheres of arbitrary radius. The calculated XRPD pattern based on the single crystal data and structure for the 1:1 tetrahydrocannabinolic acid L-proline at 100 K is shown in FIG. 4 and a comparison of this calculated/predicted XRPD pattern (top) with the high resolution XRPD pattern collected experimentally (bottom) is shown in FIG. 5. It is noted that there are some small shifts in some of the peaks owing to the fact that the experimental XRPD pattern was collected at room temperature and the calculated XRPD pattern is derived from data collected at 100 K. There are also small intensity differences owing to preferred orientation effects, present in the experimental pattern.

TABLE 3

| | |
|---|---|
| Molecular formula | $C_{27}H_{39}NO_6$ |
| Molecular weight | 473.59 |
| Crystal System | Monoclinic |
| Space Group | $P2_1$ |
| Unit Cell Dimensions | a = 12.02010(10) Å |
| | b = 5.54740(10) Å |
| | c = 19.8543(2)Å |
| | α = 90.00° |
| | β = 102.54(3)° |
| | γ = 90.00° |
| Cell Volume | 1294.53(3) $Å^3$ |
| Z | 2 |
| Temperature | 100(1) K |
| Radiation Wavelength/type | 1.54184 Å/CuKα |
| Goodness of fit | 1.022 |
| R factor | 0.0281 |
| Morphology | Colourless lath |

1.5 DSC of the 1:1 Tetrahydrocannabinolic Acid L-Proline Cocrystal

Figure 6:
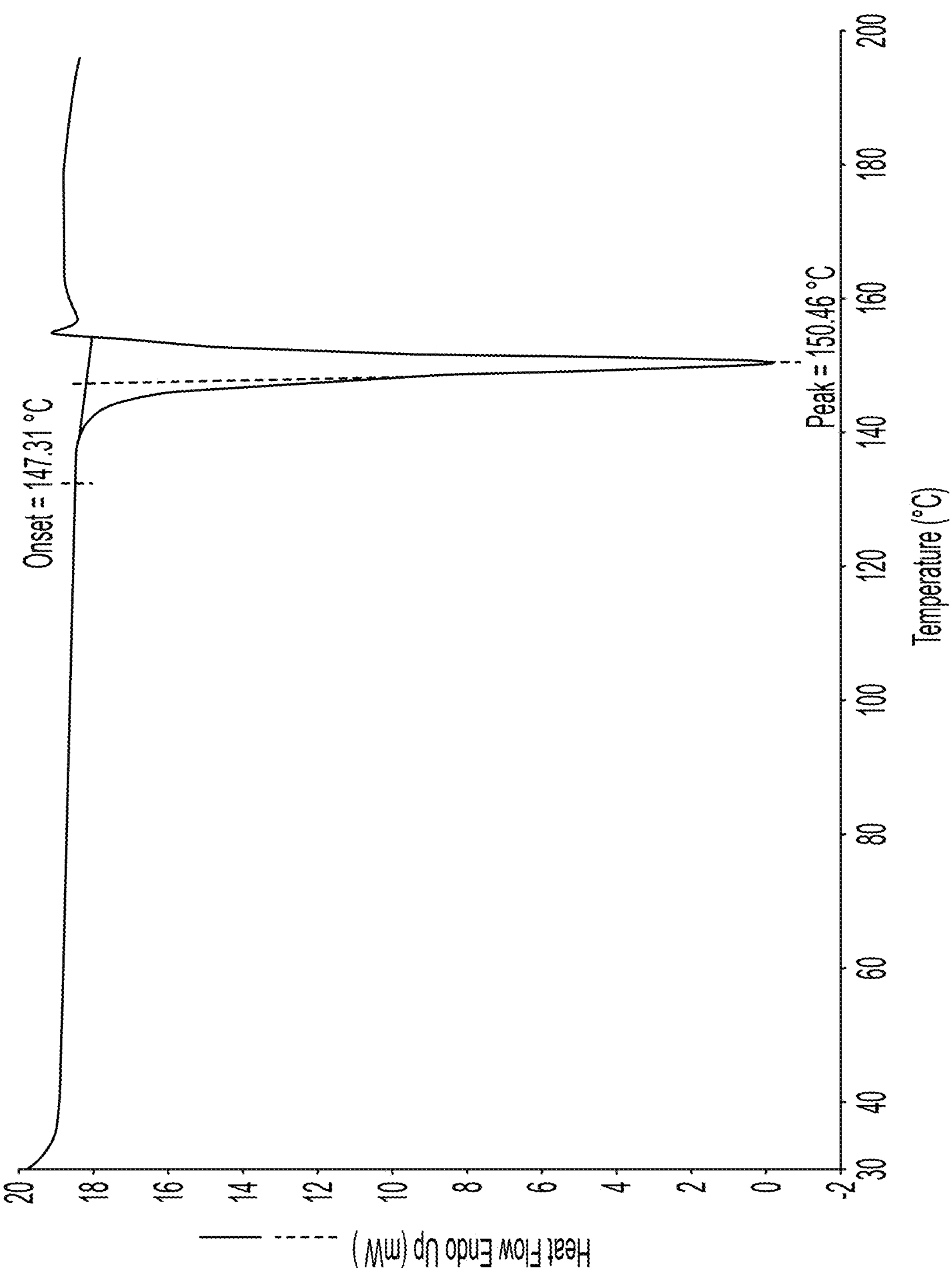
FIG. 6 shows a DSC trace for the 1:1 tetrahydrocannabinolic acid L-proline cocrystal.

The differential scanning calorimetry (DSC) trace, FIG. 6, shows a single endotherm with an onset temperature of 147.3° C. and a peak maximum of 150.5° C.

1.6 $^1$H NMR Spectrum of 1:1 Tetrahydrocannabinolic Acid L-Proline Cocrystal

Figure 7:
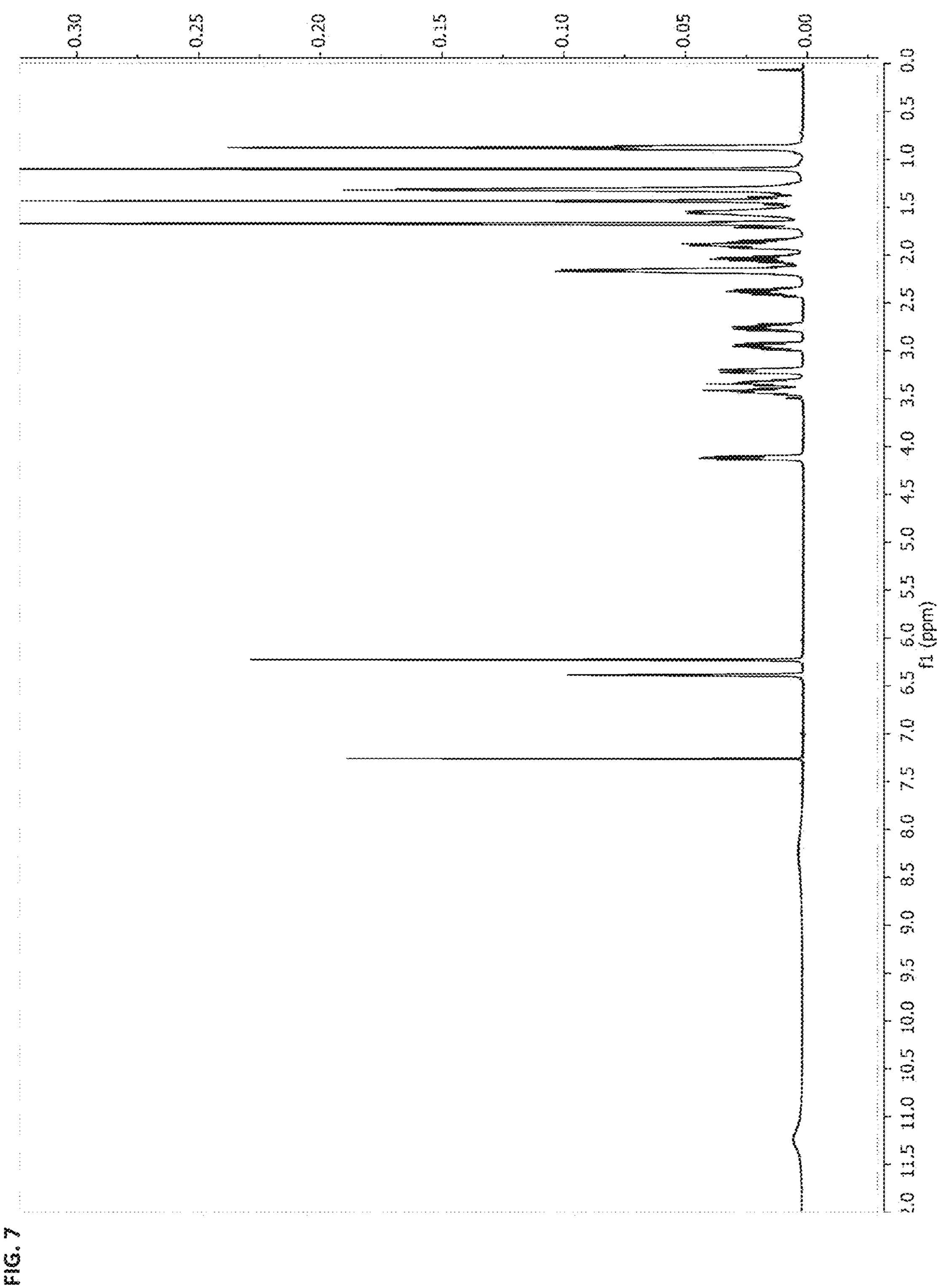
FIG. 7 shows the $^1$H NMR spectrum of 1:1 tetrahydrocannabinolic acid L-proline cocrystal.

The $^1$H NMR spectrum of the 1:1 tetrahydrocannabinolic acid L-proline cocrystal, shown in FIG. 7, displays the following peaks: $^1$H NMR (400 MHz, $CDCl_3$): δ 0.84-0.92 (3H), 1.10 (3H), 1.26-1.36 (4H), 1.38-1.48 (4H), 1.50-1.62 ppm (2), 1.63-1.74 (4H), 1.81-1.96 (2H), 1.99-2.10 (1H), 2.11-2.22 (3H), 2.32-2.44 (1H), 2.69-2.81 (1H), 2.90-3.00 (1H), 3.16-3.26 (1H), 3.28-3.38 (1H), 3.38-3.48 (1H), 4.09-4.16 (1H), 6.23 (1H) and 6.39 (1H). The peak at 4.09-4.16 ppm in the $^1$H NMR spectrum corresponds to one proton on the pyrrolidine ring of L-proline. Comparison of the integration of this peak with that at 6.23 ppm, which corresponds to one of the aromatic protons of tetrahydrocannabinolic acid, indicates that the cocrystal has an API:coformer stoichiometry of 1:1.

Example 2: 1:1 Tetrahydrocannabinolic Acid D-Proline Cocrystal 2.1 Preparation of a 1:1 Tetrahydrocannabinolic Acid D-Proline Cocrystal The batch of the 1:1 tetrahydrocannabinolic acid D-proline cocrystal used for characterisation was prepared as follows:

Tetrahydrocannabinolic acid (111 mg, 0.31 mmol) and D-proline (45 mg, 0.39 mmol) were weighed into a glass vial and methanol (1 ml) was added. The resulting white slurry was stirred at room temperature for 30 minutes and then at 5° C. for a further 3 hours. The product was then filtered under vacuum and dried under ambient conditions overnight.

Figure 8:
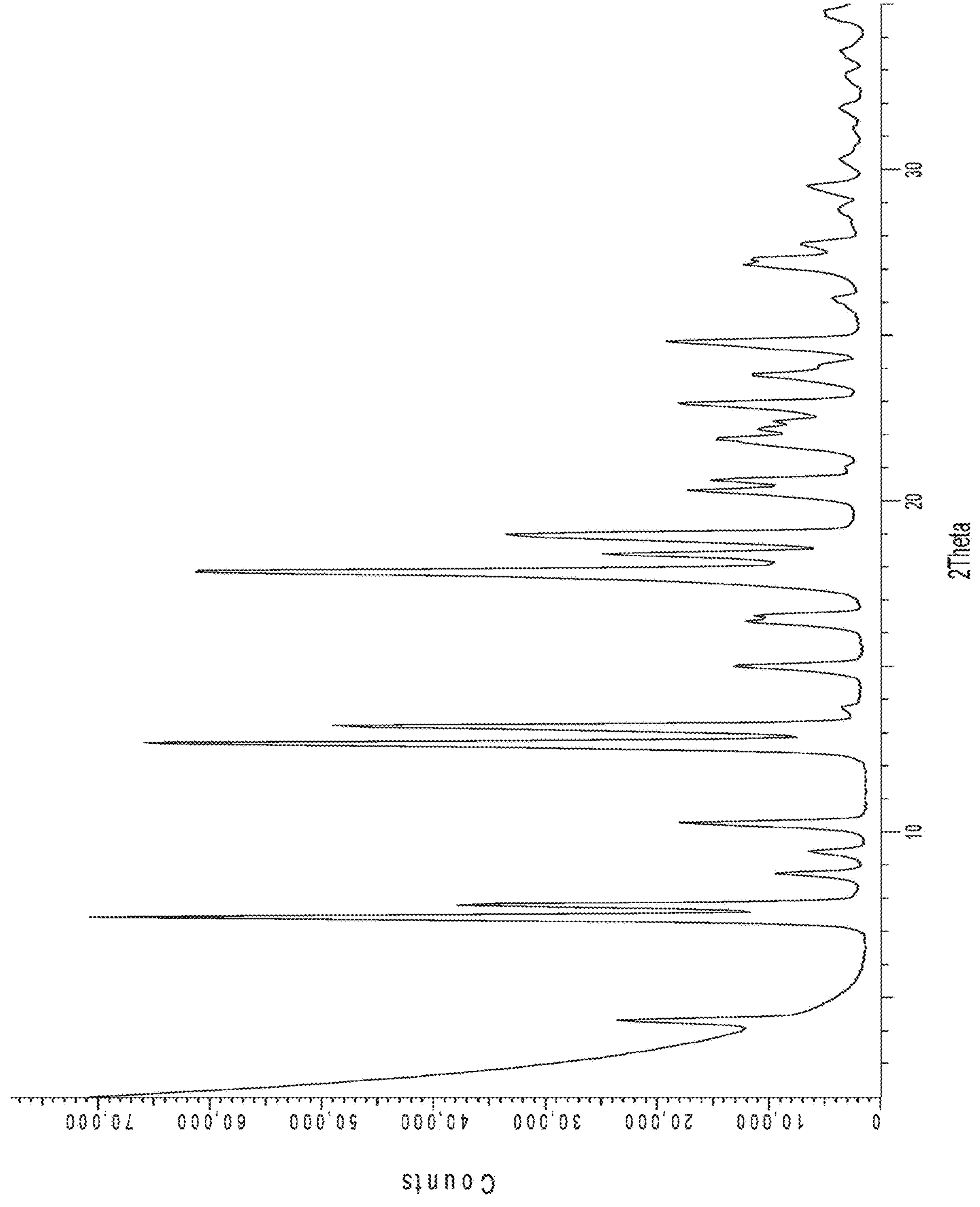
FIG. 8 shows a low resolution XRPD diagram of the 1:1 tetrahydrocannabinolic acid D-proline cocrystal.

2.2 Low Resolution XRPD Characterisation of a 1:1 Tetrahydrocannabinolic Acid D-Proline Cocrystal The low resolution experimental XRPD pattern of the 1:1 tetrahydrocannabinolic acid D-proline cocrystal is shown in FIG. 8. Table 4 lists the angles, °2θ±0.2°2θ, and d-spacing of the peaks identified in the experimental XRPD pattern of FIG. 8. The entire list of peaks, or a subset thereof, may be sufficient to characterize the cocrystal, as well as by an XRPD pattern substantially similar to FIG. 8. For example, the cocrystal may be characterized by at least two, at least three, at least four or more of the peaks in Table 4 separated from one another by ±0.2° 2θ.

TABLE 4

| Angle °2θ ± 0.2 °2θ | d value Angstrom | Intensity % |
|---|---|---|
| 4.3 | 20.43 | 15.6% |
| 7.4 | 11.88 | 100.0% |
| 7.8 | 11.32 | 51.1% |
| 8.8 | 10.10 | 11.3% |
| 9.4 | 9.39 | 7.0% |
| 10.3 | 8.61 | 23.9% |
| 12.7 | 6.97 | 97.3% |
| 13.2 | 6.70 | 71.4% |
| 13.8 | 6.43 | 2.8% |
| 15.0 | 5.89 | 17.7% |
| 16.4 | 5.41 | 15.8% |
| 17.9 | 4.96 | 94.7% |
| 18.4 | 4.82 | 36.5% |
| 19.0 | 4.67 | 49.9% |
| 20.3 | 4.37 | 24.1% |
| 20.6 | 4.30 | 21.4% |
| 21.9 | 4.06 | 20.1% |
| 22.2 | 4.01 | 14.0% |
| 23.0 | 3.87 | 25.8% |
| 23.8 | 3.73 | 15.2% |
| 24.8 | 3.59 | 28.6% |

TABLE 4-continued

| Angle °2θ ± 0.2 °2θ | d value Angstrom | Intensity % |
|---|---|---|
| 26.1 | 3.41 | 4.0% |
| 27.1 | 3.28 | 16.8% |
| 27.8 | 3.21 | 8.4% |
| 28.8 | 3.10 | 2.8% |
| 29.5 | 3.02 | 7.4% |

2.3 DSC of the 1:1 Tetrahydrocannabinolic Acid D-Proline Cocrystal

Figure 9:
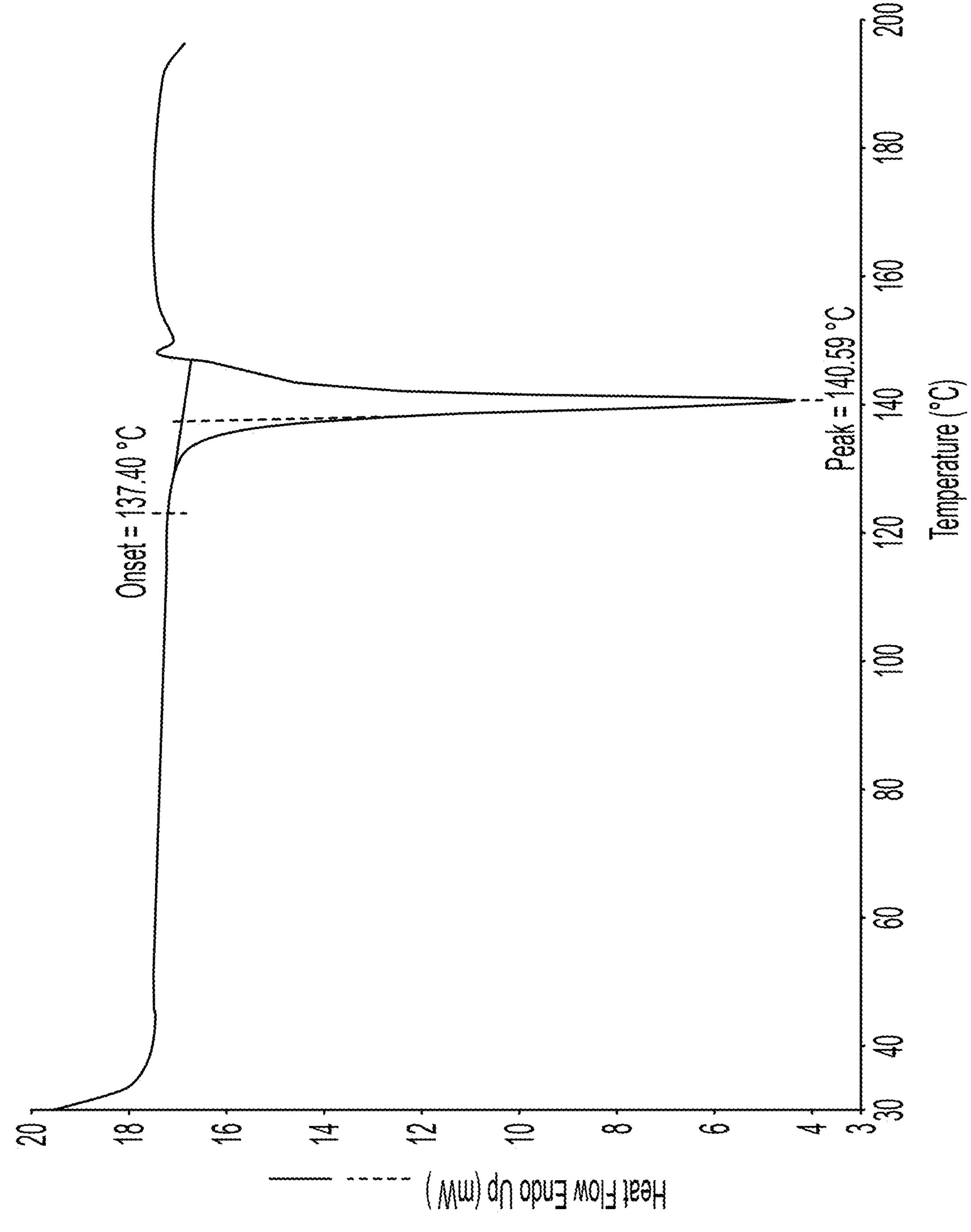
FIG. 9 shows a DSC trace for the 1:1 tetrahydrocannabinolic acid D-proline cocrystal.

The differential scanning calorimetry (DSC) trace, FIG. 9, shows a single endotherm with an onset temperature of 137.4° C. and a peak maximum of 140.6° C.

Example 3: 1:1 Tetrahydrocannabinolic Acid D,L-Proline Cocrystal

3.1 Preparation of a 1:1 Tetrahydrocannabinolic Acid D,L-Proline Cocrystal

The batch of the 1:1 tetrahydrocannabinolic acid D,L-proline cocrystal used for characterisation was prepared as follows:

Tetrahydrocannabinolic acid (101 mg, 0.28 mmol) and D,L-proline (41 mg, 0.36 mmol) were weighed into a glass vial and methanol (1 ml) was added. The resulting white slurry was stirred at room temperature for 30 minutes and then at 5° C. for a further 3 hours. The product was then filtered under vacuum and dried under ambient conditions overnight.

Figure 10:
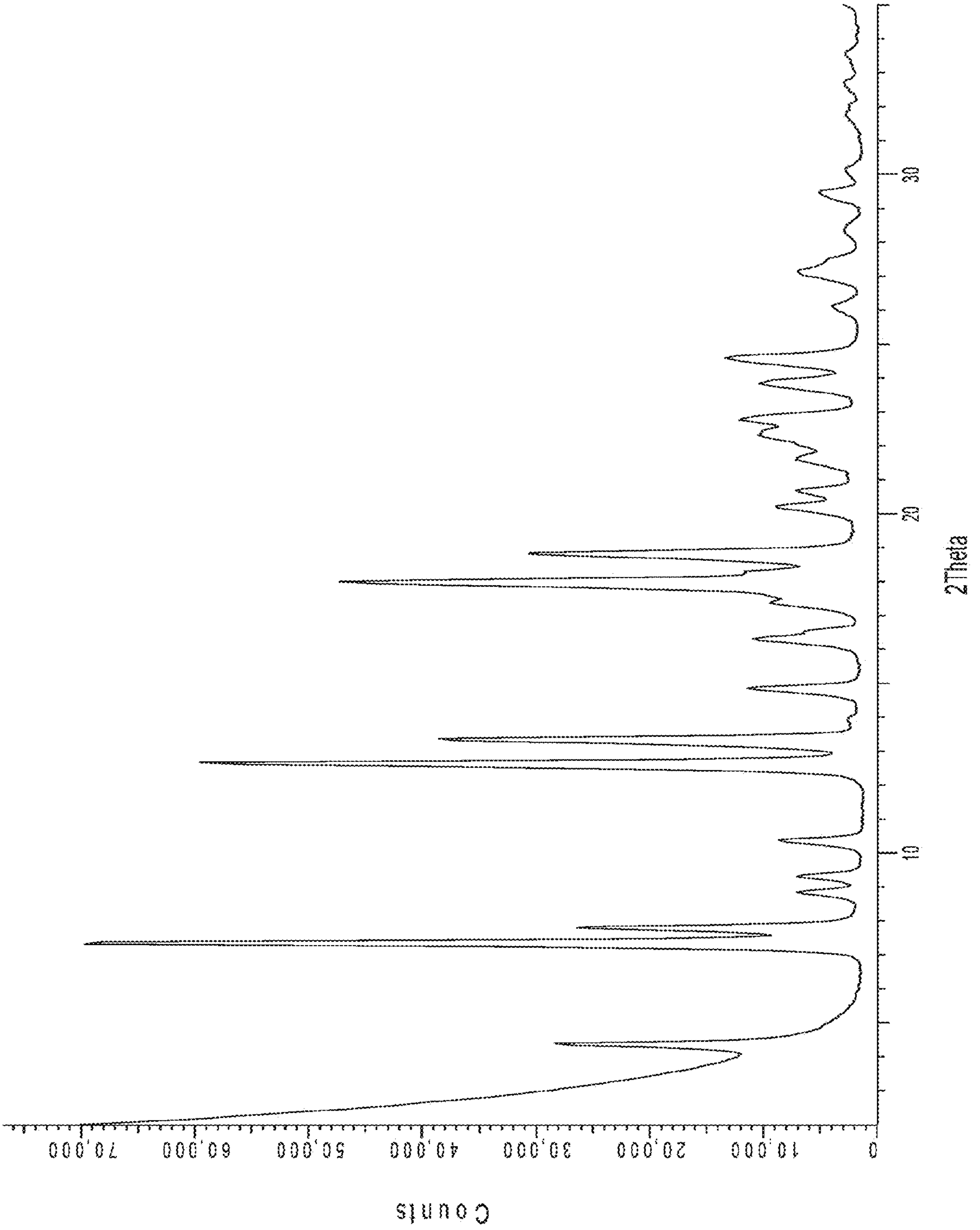
FIG. 10 shows a low resolution XRPD diagram of the 1:1 tetrahydrocannabinolic acid D,L-proline cocrystal.

3.2 Low Resolution XRPD Characterisation of a 1:1 Tetrahydrocannabinolic Acid D,L-Proline Cocrystal The experimental XRPD pattern of the 1:1 tetrahydrocannabinolic acid D,L-proline cocrystal is shown in FIG. 10. Table 5 lists the angles, °2θ±0.2°2θ, and d-spacing of the peaks identified in the experimental XRPD pattern of FIG. 10. The entire list of peaks, or a subset thereof, may be sufficient to characterize the cocrystal, as well as by an XRPD pattern substantially similar to FIG. 10.

TABLE 5

| Angle °2θ ± 0.2 °2θ | d value Angstrom | Intensity % |
|---|---|---|
| 4.4 | 20.20 | 23.5% |
| 7.4 | 12.01 | 100.0% |
| 7.8 | 11.32 | 36.2% |
| 8.8 | 9.99 | 8.0% |
| 9.3 | 9.48 | 8.1% |
| 10.4 | 8.52 | 10.9% |
| 12.6 | 6.99 | 90.8% |
| 13.4 | 6.62 | 58.4% |
| 14.9 | 5.96 | 15.8% |
| 16.3 | 5.43 | 14.7% |
| 17.4 | 5.10 | 12.3% |
| 18.0 | 4.93 | 75.3% |
| 18.8 | 4.71 | 47.9% |
| 20.2 | 4.39 | 11.3% |
| 20.7 | 4.29 | 8.3% |
| 21.6 | 4.11 | 8.3% |
| 22.3 | 3.98 | 14.1% |
| 22.8 | 3.90 | 17.1% |
| 23.8 | 3.73 | 14.4% |

TABLE 5-continued

| Angle °2θ ± 0.2 °2θ | d value Angstrom | Intensity % |
|---|---|---|
| 24.6 | 3.62 | 19.7% |
| 26.1 | 3.41 | 3.8% |
| 27.2 | 3.28 | 8.9% |
| 28.4 | 3.14 | 1.9% |
| 29.5 | 3.03 | 6.2% |

3.3 DSC of the 1:1 Tetrahydrocannabinolic Acid D,L-Proline Cocrystal

Figure 11:
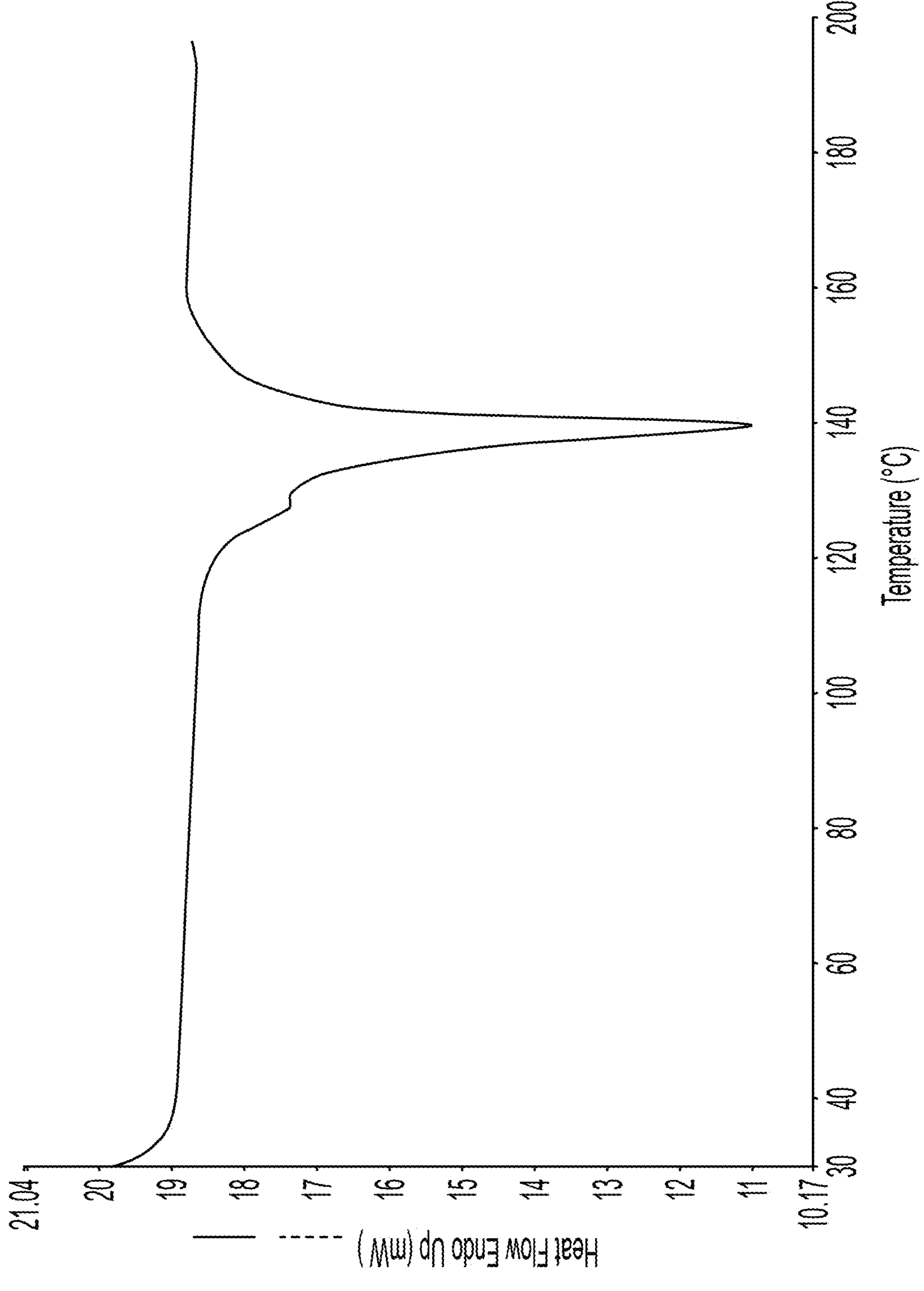
FIG. 11 shows a DSC trace for the 1:1 tetrahydrocannabinolic acid D,L-proline cocrystal.

The differential scanning calorimetry (DSC) trace, FIG. 11, shows a single endotherm with an onset temperature of 137.4° C. and a peak maximum of 140.6° C.

Example 4: 1:1 Tetrahydrocannabinolic Acid Ethyl Maltol Cocrystal

4.1 Preparation of a 1:1 Tetrahydrocannabinolic Acid Ethyl Maltol Cocrystal

The batch of the 1:1 tetrahydrocannabinolic acid ethyl maltol cocrystal used for characterisation was prepared as follows:

Tetrahydrocannabinolic acid (256 mg, 0.71 mmol) and ethyl maltol (86 mg, 0.61 mmol) were weighed into a glass vial. 2 ml of a saturated solution of ethyl maltol in nitromethane was added to the vial followed by a further 1 ml of nitromethane. The resulting slurry was placed in a shaker and matured for 24 hours (room temperature to 40° C. on an 8 hour cycle, heating to 40° C. for 4 hours and then cooling to RT for a further 4 hours). The product was then filtered under vacuum and dried under ambient conditions overnight.

Figure 12:
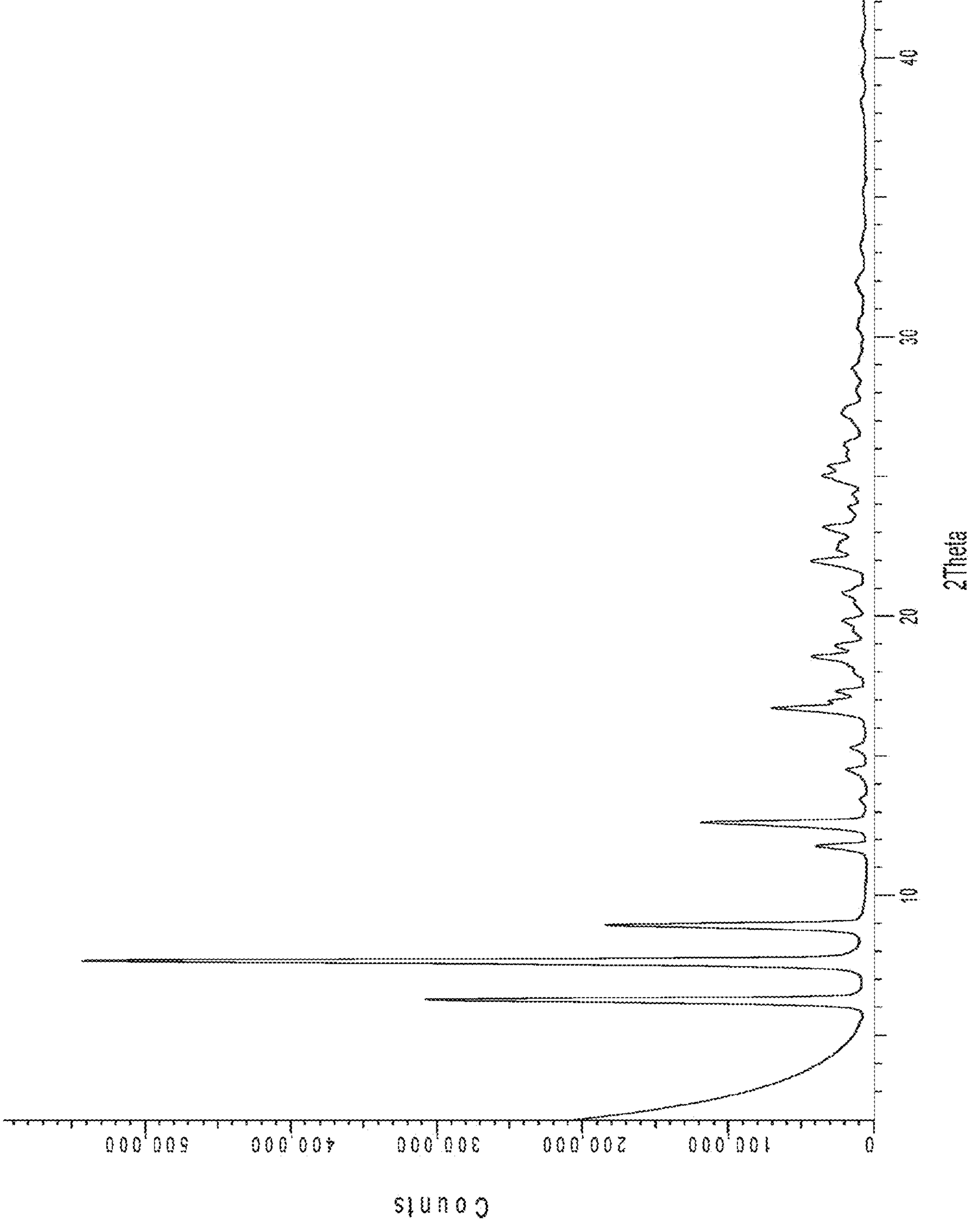
FIG. 12 shows a low resolution XRPD diagram of the 1:1 tetrahydrocannabinolic acid ethyl maltol cocrystal.

4.2 Low Resolution XRPD Characterisation of a 1:1 Tetrahydrocannabinolic Acid Ethyl Maltol Cocrystal The low resolution experimental XRPD pattern of the 1:1 tetrahydrocannabinolic acid ethyl maltol cocrystal is shown in FIG. 12. Table 6 lists the angles, °26±0.2°2θ, and d-spacing of the peaks identified in the experimental XRPD pattern of FIG. 12. The entire list of peaks, or a subset thereof, may be sufficient to characterize the cocrystal, as well as by an XRPD pattern substantially similar to FIG. 12. For example, the cocrystal may be characterized by at least two, at least three, at least four or more of the peaks in Table 6 separated from one another by ±0.2°2θ.

TABLE 6

| Angle °2θ ± 0.2 °2θ | d value Angstrom | Intensity % |
|---|---|---|
| 6.3 | 14.06 | 54.2% |
| 7.7 | 11.52 | 100.0% |
| 8.9 | 9.88 | 34.0% |
| 11.8 | 7.51 | 6.9% |
| 12.6 | 7.01 | 22.1% |
| 13.5 | 6.57 | 1.2% |
| 14.5 | 6.09 | 2.6% |
| 15.3 | 5.78 | 2.1% |
| 16.7 | 5.30 | 12.6% |
| 17.0 | 5.22 | 4.9% |
| 17.3 | 5.12 | 3.9% |

TABLE 6-continued

| Angle °2θ ± 0.2 °2θ | d value Angstrom | Intensity % |
|---|---|---|
| 18.6 | 4.78 | 6.9% |
| 18.9 | 4.68 | 3.8% |
| 19.8 | 4.47 | 2.9% |
| 20.8 | 4.26 | 2.8% |
| 22.0 | 4.04 | 6.9% |
| 22.5 | 3.96 | 3.1% |
| 22.6 | 3.93 | 3.0% |
| 23.2 | 3.83 | 5.1% |
| 25.0 | 3.55 | 5.3% |
| 25.4 | 3.50 | 4.5% |
| 26.1 | 3.41 | 2.3% |
| 27.3 | 3.26 | 2.7% |

Figure 13:
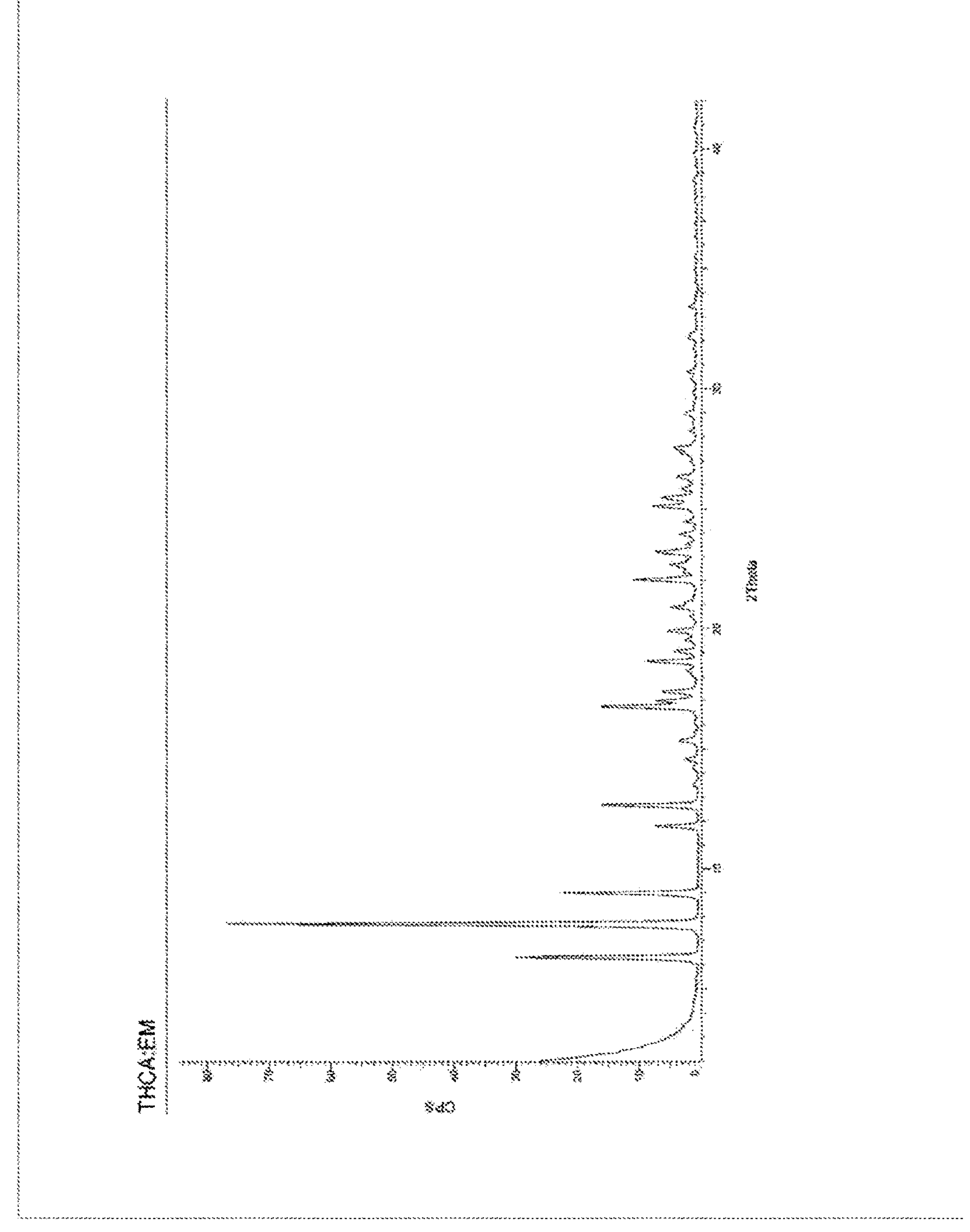
FIG. 13 shows a high resolution XRPD diagram of the 1:1 tetrahydrocannabinolic acid ethyl maltol cocrystal.

4.3 High Resolution XRPD Characterisation of a 1:1 Tetrahydrocannabinolic Acid Ethyl Maltol Cocrystal The high resolution experimental XRPD pattern of the 1:1 tetrahydrocannabinolic acid ethyl maltol cocrystal is shown in FIG. 13. Table 7 lists the angles, +26±0.2°2Θ, and d-spacing of the peaks identified in the experimental XRPD pattern of FIG. 13. The entire list of peaks, or a subset thereof, may be sufficient to characterize the cocrystal, as well as by an XRPD pattern substantially similar to FIG. 13. For example, the cocrystal may be characterized by at least two, at least three, at least four or all of the peaks selected from the peaks at 6.3, 7.7, 9.0, 11.8 and 12.7°2θ±0.2°2θ.

TABLE 7

| Angle °2θ ± 0.2 °2θ | d value Angstrom | Intensity % |
|---|---|---|
| 6.3 | 14.01 | 38% |
| 7.7 | 11.48 | 100% |
| 9.0 | 9.83 | 29% |
| 11.8 | 7.50 | 10% |
| 12.7 | 6.99 | 23% |
| 14.2 | 6.21 | 1% |
| 14.6 | 6.07 | 3% |
| 15.4 | 5.77 | 4% |
| 16.8 | 5.29 | 33% |
| 17.0 | 5.21 | 14% |
| 17.4 | 5.10 | 8% |
| 18.3 | 4.85 | 3% |
| 18.6 | 4.76 | 12% |
| 19.0 | 4.66 | 5% |
| 19.5 | 4.54 | 2% |
| 19.9 | 4.46 | 6% |
| 20.5 | 4.33 | 1% |
| 20.9 | 4.25 | 6% |
| 22.0 | 4.03 | 16% |
| 22.7 | 3.92 | 9% |
| 23.2 | 3.83 | 9% |
| 24.0 | 3.71 | 4% |
| 24.5 | 3.63 | 3% |
| 25.1 | 3.54 | 10% |
| 25.5 | 3.49 | 8% |
| 25.9 | 3.44 | 3% |
| 26.3 | 3.38 | 4% |
| 27.5 | 3.24 | 7% |

4.4 DSC of the 1:1 Tetrahydrocannabinolic Acid Ethyl Maltol Cocrystal

Figure 14:
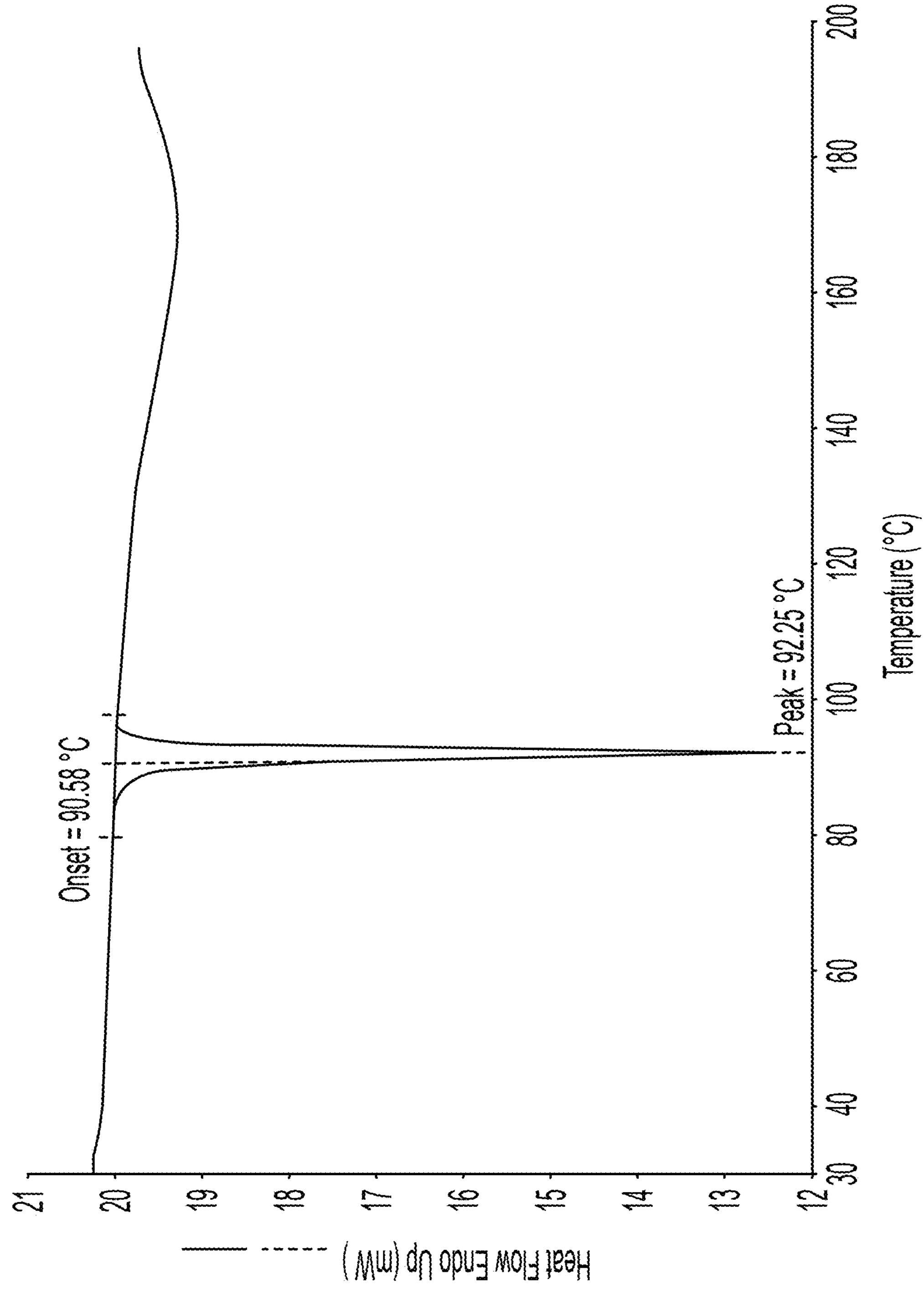
FIG. 14 shows a DSC trace for the 1:1 tetrahydrocannabinolic acid ethyl maltol cocrystal.

The differential scanning calorimetry (DSC) trace, FIG. 14, shows a major endotherm with a peak maximum of 139.8 that shows a minor shoulder around 128° C.

Figure 15:
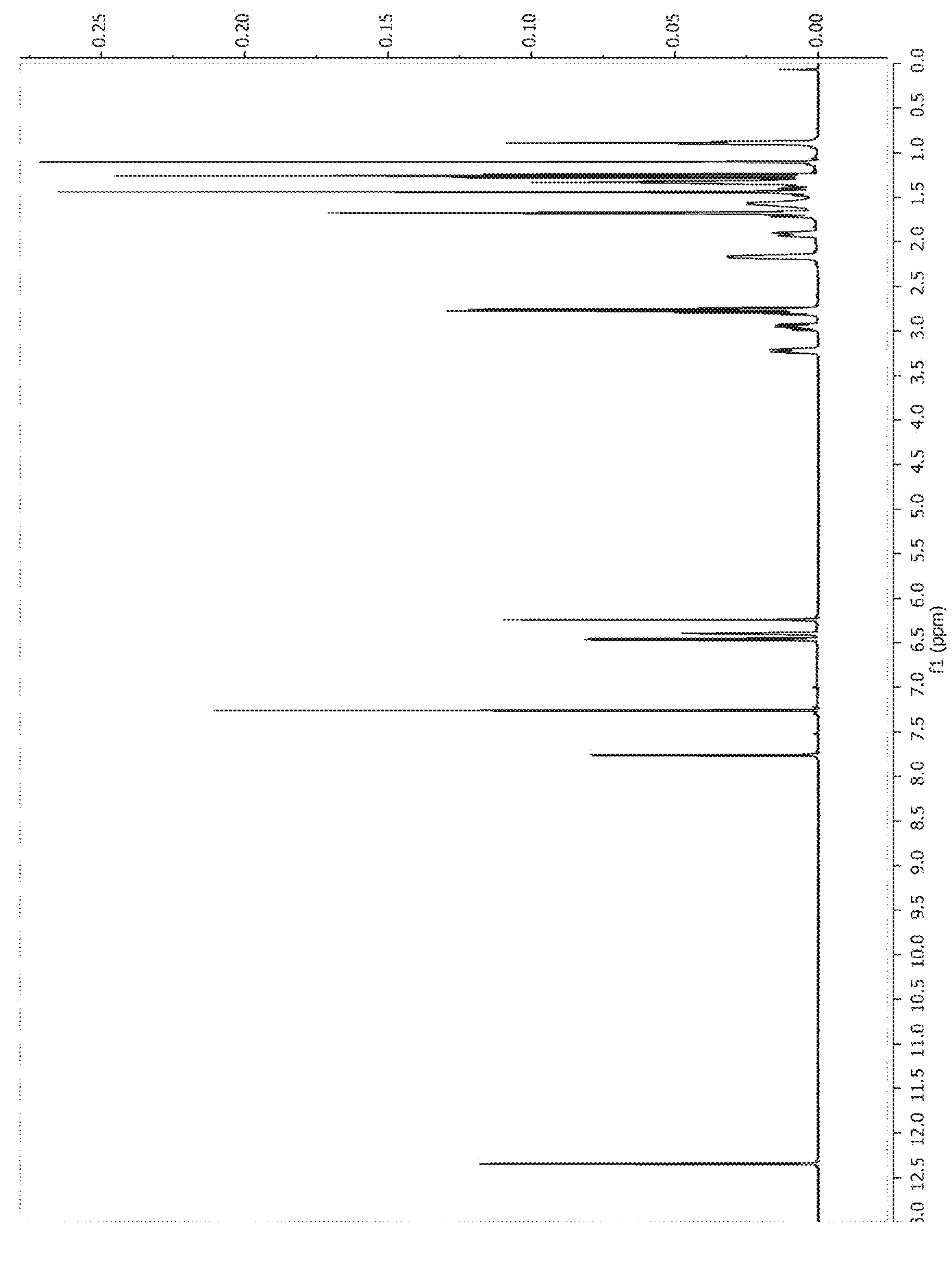
FIG. 15 shows the $^1$H NMR spectrum of 1:1 tetrahydrocannabinolic acid ethyl maltol cocrystal.

4.5 $^{1}H$ NMR Spectrum of 1:1 Tetrahydrocannabinolic Acid Ethyl Maltol Cocrystal The $^{1}H$ NMR spectrum of the 1:1 tetrahydrocannabinolic acid ethyl maltol cocrystal, shown in FIG. 15, displays the following peaks: $^{1}H$ NMR (400 MHz, $CDCl_3$): δ 0.85-0.93 (3H), 1.11 (3H), 1.23-1.29 (4H), 1.29-1.39 (4H), 1.40-1.48 (4H), 1.51-1.63 (2H), 1.64-1.74 (4H), 1.88-1.96 (1H), 2.13-2.21 (1H), 2.72-2.84 (3H), 2.90-3.00 (1H), 3.18-3.28 (1H), 6.24 (1H), 6.39 (1H), 6.44-6.48 (1H), 7.74-7.78 (1H) and 12.35 (1H). The peak at 7.74-7.78 ppm in the $^{1}H$ NMR spectrum corresponds to one proton on the pyranone ring of ethyl maltol. Comparison of the integration of this peak with that at 6.24 ppm, which corresponds to one of the aromatic protons of tetrahydrocannabinolic acid, indicates that the cocrystal has an API:coformer stoichiometry of 1:1.

Example 5: 1:1 Tetrahydrocannabinolic Acid Caffeine Cocrystal

5.1 Preparation of a 1:1 Tetrahydrocannabinolic Acid Caffeine Cocrystal

The batch of the 1:1 tetrahydrocannabinolic acid caffeine cocrystal used for characterisation was prepared as follows:

Tetrahydrocannabinolic acid (83 mg, 0.23 mmol) and caffeine (45 mg, 0.23 mmol) were milled together with methanol (1 drop) for 4×15 minutes at 30 Hz in a Retsch MM400 ball mill. The product was dried under ambient conditions overnight and then in vacuo at 40° C. for 1 hr.

Figure 16:
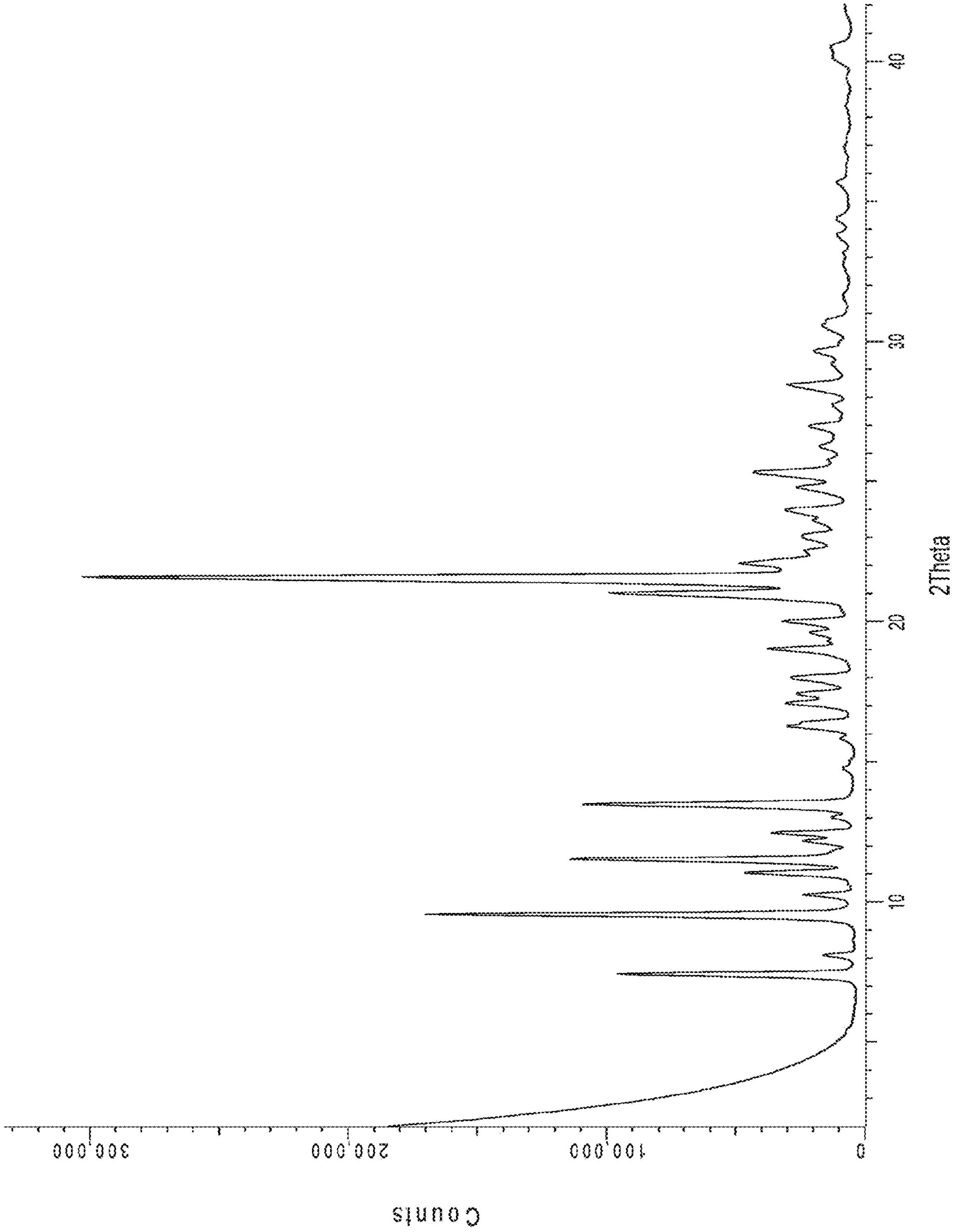
FIG. 16 shows a low resolution XRPD diagram of the 1:1 tetrahydrocannabinolic acid caffeine cocrystal.

5.2 Low Resolution XRPD Characterisation of a 1:1 Tetrahydrocannabinolic Acid Caffeine Cocrystal The low resolution experimental XRPD pattern of the 1:1 tetrahydrocannabinolic acid caffeine cocrystal is shown in FIG. 16. Table 8 lists the angles, °2θ±0.2°2θ, and d-spacing of the peaks identified in the experimental XRPD pattern of FIG. 16. The entire list of peaks, or a subset thereof, may be sufficient to characterize the cocrystal, as well as by an XRPD pattern substantially similar to FIG. 16. For example, the cocrystal may be characterized by at least two, at least three, at least four or more of the peaks in Table 8 separated from one another by ±0.2°2θ.

TABLE 8

| Angle °2θ ± 0.2 °2θ | d value Angstrom | Intensity % |
|---|---|---|
| 7.4 | 11.88 | 29.0% |
| 8.1 | 10.90 | 3.9% |
| 9.6 | 9.24 | 54.5% |
| 10.3 | 8.61 | 6.4% |
| 11.1 | 8.00 | 13.8% |
| 11.5 | 7.67 | 36.5% |
| 12.2 | 7.26 | 6.4% |
| 12.5 | 7.09 | 10.4% |
| 13.0 | 6.79 | 2.8% |
| 13.5 | 6.56 | 34.8% |
| 16.3 | 5.44 | 8.4% |
| 17.1 | 5.18 | 8.4% |
| 17.4 | 5.08 | 6.7% |
| 18.0 | 4.92 | 7.5% |
| 19.0 | 4.66 | 10.3% |
| 19.6 | 4.52 | 4.9% |
| 20.0 | 4.43 | 8.4% |
| 21.0 | 4.22 | 30.3% |
| 21.6 | 4.11 | 100.0% |
| 22.1 | 4.02 | 13.6% |

TABLE 8-continued

| Angle °2θ ± 0.2 °2θ | d value Angstrom | Intensity % |
|---|---|---|
| 22.5 | 3.94 | 5.1% |
| 23.0 | 3.86 | 5.2% |
| 23.6 | 3.76 | 4.0% |
| 24.0 | 3.71 | 7.5% |
| 24.8 | 3.59 | 6.0% |
| 25.3 | 3.51 | 11.5% |
| 25.8 | 3.45 | 2.0% |
| 26.3 | 3.39 | 2.9% |
| 27.0 | 3.30 | 4.4% |
| 28.5 | 3.13 | 7.4% |
| 29.7 | 3.01 | 4.1% |
| 30.6 | 2.92 | 3.2% |

Figure 17:
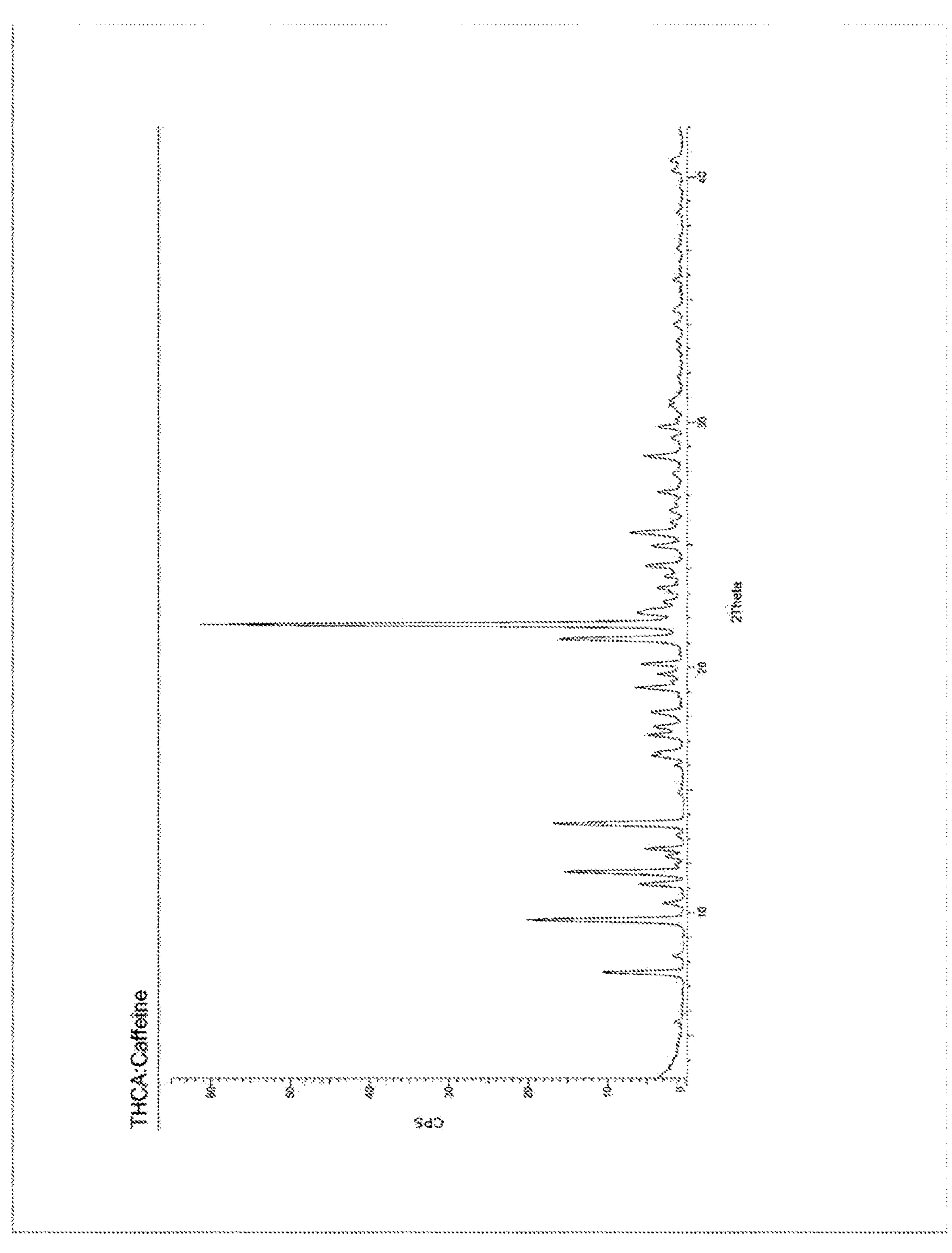
FIG. 17 shows a high resolution XRPD diagram of the 1:1 tetrahydrocannabinolic acid caffeine cocrystal.

5.3 High Resolution XRPD Characterisation of a 1:1 Tetrahydrocannabinolic Acid Caffeine Cocrystal The high resolution experimental XRPD pattern of the 1:1 tetrahydrocannabinolic acid caffeine cocrystal is shown in FIG. 17. Table 9 lists the angles, °2θ±0.2°2θ, and d-spacing of the peaks identified in the experimental XRPD pattern of FIG. 17. The entire list of peaks, or a subset thereof, may be sufficient to characterize the cocrystal, as well as by an XRPD pattern substantially similar to FIG. 17. For example, the cocrystal may be characterized by at least two, at least three, at least four or all of the peaks selected from the peaks at 7.6, 8.2, 9.7, 10.4, 13.6 and 18.2°2θ±0.2°2θ.

TABLE 9

| Angle °2θ ± 0.2 °2θ | d value Angstrom | Intensity % |
|---|---|---|
| 8.2 | 10.72 | 2% |
| 9.7 | 9.11 | 29% |
| 10.4 | 8.51 | 4% |
| 11.2 | 7.90 | 8% |
| 11.7 | 7.59 | 23% |
| 12.3 | 7.19 | 3% |
| 12.6 | 7.02 | 7% |
| 13.1 | 6.73 | 1% |
| 13.6 | 6.49 | 24% |
| 16.0 | 5.54 | 2% |
| 16.4 | 5.40 | 5% |
| 16.5 | 5.36 | 8% |
| 17.2 | 5.14 | 7% |
| 17.6 | 5.04 | 5% |
| 18.2 | 4.88 | 6% |
| 19.2 | 4.62 | 9% |
| 19.7 | 4.49 | 5% |
| 20.1 | 4.40 | 8% |
| 21.2 | 4.20 | 25% |
| 21.7 | 4.08 | 100% |
| 22.2 | 3.99 | 8% |
| 22.6 | 3.92 | 3% |
| 23.2 | 3.82 | 5% |
| 23.7 | 3.74 | 3% |
| 24.1 | 3.68 | 7% |
| 25.0 | 3.56 | 6% |
| 25.5 | 3.49 | 11% |
| 25.9 | 3.44 | 2% |
| 26.4 | 3.37 | 2% |
| 27.1 | 3.28 | 5% |
| 27.9 | 3.20 | 1% |
| 28.6 | 3.12 | 8% |
| 29.4 | 3.04 | 2% |
| 29.8 | 2.99 | 5% |

5.5 DSC of the 1:1 Tetrahydrocannabinolic Acid Caffeine Cocrystal

Figure 18:
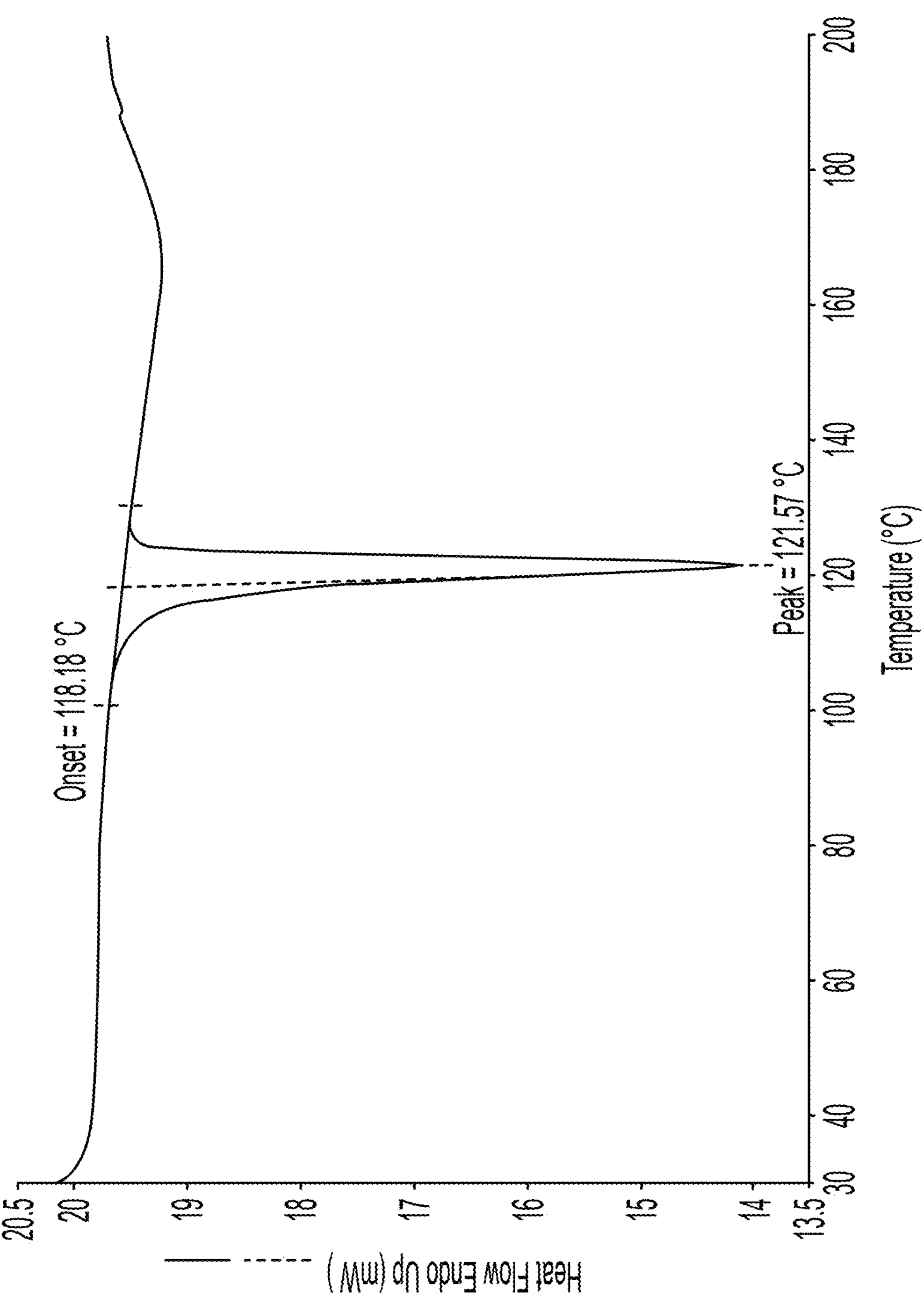
FIG. 18 shows a DSC trace for the 1:1 tetrahydrocannabinolic acid caffeine cocrystal.

The differential scanning calorimetry (DSC) trace, FIG. 18, shows a single endotherm with an onset temperature of 118.2° C. and a peak maximum of 121.6° C.

Example 6: Solid-State Stability Study for the Tetrahydrocannabinolic Acid Cocrystals A study was carried out to examine the physical stability of the tetrahydrocannabinolic acid cocrystals with respect to solid form conversion or signs of decomposition over time under both ambient and accelerated conditions. 50 mg each of the 1:1 tetrahydrocannabinolic acid L-proline cocrystal, 1:1 tetrahydrocannabinolic acid ethyl maltol cocrystal and 1:1 tetrahydrocannabinolic acid caffeine cocrystal were separately placed in a sealed container at 40° C. and 75% relative humidity and stored under these conditions for 14 days. After this time all samples remained as white solids with no signs of deliquescence and no signs of any colour change, which would be a typical indication of THC formation or decomposition. Each sample was analysed by XRPD to observe any potential form changes and the results of the study are shown in Table 10.

TABLE 10

| | 40° C./75% RH-2 weeks | |
|---|---|---|
| Cocrystal | Appearance | XRPD analysis |
| 1:1 THCA L-PROLINE | No change | No change (as FIG. 1) |
| 1:1 THCA ETHYL MALTOL | No change | Slight signs of cocrystal dissociation |
| 1:1 THCA CAFFEINE | No change | No change (as FIG. 13) |

A second stability study was carried out where 50 mg each of the 1:1 tetrahydrocannabinolic acid L-proline cocrystal, 1:1 tetrahydrocannabinolic acid ethyl maltol cocrystal and 1:1 tetrahydrocannabinolic acid caffeine cocrystal were separately placed in a clear glass vial which was then stored under ambient conditions for 6 months. After this time all the cocrystals remained as white solids with no signs of colour change. Each sample was analysed by XRPD to observe any potential form changes and the results of the study are shown in Table 11.

TABLE 11

| | Ambient Conditions-6 months | |
|---|---|---|
| Cocrystal | Appearance | XRPD analysis |
| 1:1 THCA L-PROLINE | No change | No change (as FIG. 1) |
| 1:1 THCA ETHYL MALTOL | No change | No change (as FIG. 10) |
| 1:1 THCA CAFFEINE | No change | No change (as FIG. 13) |

It can be seen from Table 11 that after 6 month storage under ambient conditions all of the cocrystals retained their original crystalline form and that none of the tetrahydrocannabinolic acid cocrystals of this invention undergo solid form conversion or dissociation under these conditions. Whereas, as shown in Table 10, storage under accelerated conditions of 40° C. and 75% relative humidity resulted in the 1:1 tetrahydrocannabinolic acid ethyl maltol cocrystal showing slight signs of dissociation into tetrahydrocannabinolic acid and ethyl maltol, the 1:1 tetrahydrocannabinolic acid L-proline cocrystal and 1:1 tetrahydrocannabinolic acid caffeine cocrystal retained their original crystalline form and did not undergo solid form conversion or dissociation under these conditions.

The claimed invention is:

1. A tetrahydrocannabinolic acid cocrystal selected from the group of a 1:1 tetrahydrocannabinolic acid L-proline cocrystal, a 1:1 tetrahydrocannabinolic acid D-proline cocrystal, a 1:1 tetrahydrocannabinolic acid D,L-proline cocrystal, a 1:1 tetrahydrocannabinolic acid ethyl maltol cocrystal and a 1:1 tetrahydrocannabinolic acid caffeine cocrystal.

2. A tetrahydrocannabinolic acid cocrystal of claim 1, wherein the cocrystal is a 1:1 tetrahydrocannabinolic acid L-proline cocrystal characterized by:

at least two, at least three, at least four or all of the peaks selected from the peaks at 4.5, 10.5, 12.8, 13.5, 15.0 and 19.0° 2θ±0.2° 2θ;

a monoclinic $P2_1$ crystal system space group at a temperature of about 100K;

unit cell dimensions of a=12.02010(10) Å, b=5.54740(10) Å, c=19.8543(2) Å, α=90.00°, β=102.54(3)°, and γ=90.00°;

an X-ray powder diffraction pattern substantially similar to FIG. 1;

an X-ray powder diffraction pattern substantially similar to FIG. 2;

an X-ray powder diffraction pattern substantially similar to FIG. 4; or a differential scanning calorimetry trace substantially similar to FIG. 6.

3. A tetrahydrocannabinolic acid cocrystal of claim 1, wherein the cocrystal is a 1:1 tetrahydrocannabinolic acid D-proline cocrystal characterized by:

an X-ray powder diffraction pattern substantially similar to FIG. 8; or a differential scanning calorimetry trace substantially similar to FIG. 9.

4. A tetrahydrocannabinolic acid cocrystal of claim 1, wherein the cocrystal is a 1:1 tetrahydrocannabinolic acid D,L-proline cocrystal, characterized by:

an X-ray powder diffraction pattern substantially similar to FIG. 10; or a differential scanning calorimetry trace substantially similar to FIG. 11.

5. A tetrahydrocannabinolic acid cocrystal of claim 1, wherein the cocrystal is a 1:1 tetrahydrocannabinolic acid ethyl maltol cocrystal characterized by:

at least two, at least three, at least four or all of the peaks selected from the peaks at 6.3, 7.7, 9.0, 11.8 and 12.7° 2θ±0.2° 2θ;

an X-ray powder diffraction pattern substantially similar to FIG. 12;

an X-ray powder diffraction pattern substantially similar to FIG. 13; or a differential scanning calorimetry trace substantially similar to FIG. 14.

6. A tetrahydrocannabinolic acid cocrystal of claim 1, wherein the cocrystal is a 1:1 tetrahydrocannabinolic acid caffeine cocrystal characterized by:

at least two, at least three, at least four or all of the peaks selected from the peaks at 7.6, 8.2, 9.7, 10.4, 13.6 and 18.2° 2θ±0.2° 2θ;

an X-ray powder diffraction pattern substantially similar to FIG. 16;

an X-ray powder diffraction pattern substantially similar to FIG. 17; or a differential scanning calorimetry trace substantially similar to FIG. 18.

7. A pharmaceutical composition comprising a tetrahydrocannabinolic acid cocrystal according to any one of claims 1-6 and a pharmaceutically acceptable carrier.

* * * * *